under 35 U.S.C. 154(b) by 16 days.

(12) United States Patent
Harada et al.

(10) Patent No.: US 7,304,175 B2
(45) Date of Patent: Dec. 4, 2007

(54) SALT SUITABLE FOR AN ACID GENERATOR AND A CHEMICALLY AMPLIFIED RESIST COMPOSITION CONTAINING THE SAME

(75) Inventors: Yukako Harada, Settu (JP); Ichiki Takemoto, Kawanishi (JP); Kouji Toishi, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 16 days.

(21) Appl. No.: 11/353,010

(22) Filed: Feb. 14, 2006

(65) Prior Publication Data

US 2006/0194982 A1 Aug. 31, 2006

(30) Foreign Application Priority Data

Feb. 16, 2005 (JP) .............................. 2005-038855

(51) Int. Cl.
*C07C 69/00* (2006.01)
(52) U.S. Cl. .......................... 560/129; 560/1; 560/150; 430/270.1
(58) Field of Classification Search .................... 560/1, 560/129, 150; 430/270.1
See application file for complete search history.

(56) References Cited

U.S. PATENT DOCUMENTS 6,893,792 B2    5/2005   Miya et al.

2003/0194639 A1    10/2003   Miya et al.

FOREIGN PATENT DOCUMENTS

JP       2004-117959 A      4/2004

*Primary Examiner*—Yvonne Eyler
*Assistant Examiner*—Sudhakar Katakam
(74) *Attorney, Agent, or Firm*—Birch, Stewart, Kolasch & Birch, LLP

(57) ABSTRACT

The present invention provides a salt of the formula (I)

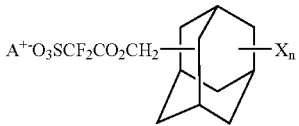

(I)

wherein X represents —OH or —Y—OH, n shows an integer of 1 to 9, $A^+$ represents an organic counter ion, Y represents a divalent saturated aliphatic hydrocarbon group having 1 to 6 carbon atoms.

The present invention also provides a chemically amplified resist composition comprising the salt of the formula (I).

15 Claims, No Drawings

SALT SUITABLE FOR AN ACID GENERATOR AND A CHEMICALLY AMPLIFIED RESIST COMPOSITION CONTAINING THE SAME

This nonprovisional application claims priority under 35 U.S.C. § 119(a) on Patent Application No. 2005-38855 filed in JAPAN on Feb. 16, 2005, the entire contents of which are hereby incorporated by reference.

FIELD OF THE INVENTION

The present invention relates to a salt suitable for an acid generator used for a chemical amplification type resist which is used in fine processing of semiconductors, and a chemically amplified resist composition containing the salt.

BACKGROUND OF THE INVENTION

Semiconductor microfabrication employs a lithography process using a resist composition containing (meth)acrylic resin component having alicyclic hydrocarbon skeletal structure such as adamantyl group (for example, JPH04-39665-A, JPH05-346668-A, JPH07-234511-A, JPH10-319595-A, etc.).

In lithography, theoretically, the shorter the expose wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. $F_2$ excimer laser having a wavelength of 157 nm seems to be the next-generation exposure light source. Further, as the exposure light source of the subsequent generation, soft X ray (EUV) having a wavelength of 13 nm or shorter has been proposed as the exposure light source following the 157 nm-wavelength $F_2$ excimer laser.

When light sources used for KrF excimer laser or those having shorter wave length are used, it is necessary to enhance the sensitivity of resists. Therefore, chemically amplified resists utilizing the catalytic action of an acid generated by exposure and containing a resin having a group being dissociated by the acid.

In lithography process utilizing such a shorter wavelength, improvement of pattern profiles has become important subject as line-widths become narrower (e.g. Proc. of SPIE Vol. 5038 (2003), 689-698).

Recently, it has been reported that resist composition with high transparency, good sensitivity and high resolution can be obtained when triphenylsulfonium 1-adamantylmethoxycarbonyldifluoromethansulfonate, p-tolyldiphenylsulfonium perfluorooctanesulfonate, and the like are used as an acid generator (e.g. JP2004-4561-A).

SUMMARY OF THE INVENTION

Objects of the present invention are to provide a salt suitable for an acid generator capable of giving resists having better resolution than conventional resist and having improved pattern profiles, and to provide an acid generator containing the salt.

Another object of the present invention are to provide synthetic intermediates for the salts and to provide a process for producing the synthetic intermediates or the salts.

Still another objects of the present invention are to provide a polymer composition containing the salts and to provide a chemically amplified resist polymer composition containing the salts.

These and other object of the present invention will be apparent from the following description.

The present invention relates to the followings:

<1> A salt of the formula (I)

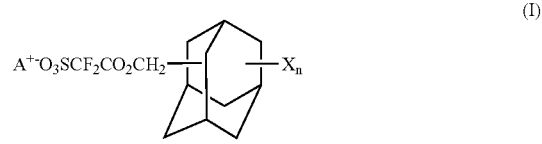

wherein X represents —OH or —Y—OH, n shows an integer of 1 to 9, $A^+$ represents an organic counter ion, Y represents a divalent saturated aliphatic hydrocarbon group having 1 to 6 carbon atoms. Hereinafter, the salt of the formula (I) may also be referred to as Salt (I).

<2> The salt according to <1>, wherein $A^+$ is at least one cation selected from the group consisting of the formulae (IIa), (IIb), (IIc) and (IId).

A cation of the formula (IIa)

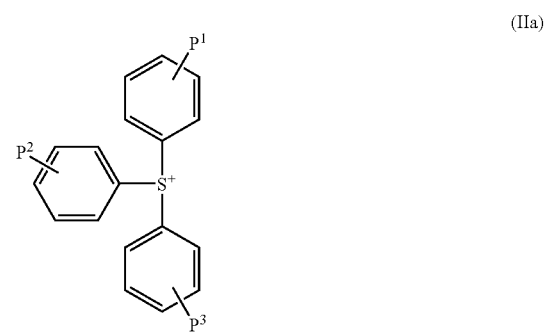

wherein $P^1$ to $P^3$ each independently represent hydrogen atom, hydroxyl group, alkyl group having 1 to 12 carbon atoms or alkoxy group having 1 to 12 carbon atoms.

A cation of the formula (IIb)

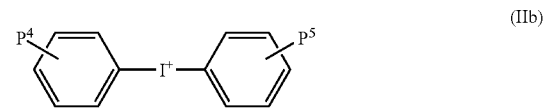

wherein $P^4$ and $P^5$ each independently represent hydrogen atom, hydroxyl group, alkyl group having 1 to 12 carbon atoms or alkoxy group having 1 to 12 carbon atoms.

A cation of the formula (IIc)

wherein $P^6$ and $P^7$ each independently represent alkyl having 1 to 12 carbon atoms or cycloalkyl having 3 to 12 carbon atoms, or $P^6$ and $P^7$ bond to form divalent acyclic hydrocarbon group having 3 to 12 carbon atoms which forms a ring together with the adjacent $S^+$, and at least one —$CH_2$— in the divalent acyclic hydrocarbon group is optionally substituted by —CO—, —O— or —S—, $P^8$ represents hydrogen, $P^9$ represents alkyl having 1 to 12 carbon atoms, cycloalkyl having 3 to 12 carbon atoms or aromatic ring group optionally substituted, or P⁸ and P⁹ bond to form divalent acyclic hydrocarbon which forms 2-oxocycloalkyl together with the adjacent —CHCO—, and at least one —CH₂— in the divalent acyclic hydrocarbon group is optionally substituted by —CO—, —O— or —S—.

A cation of the formula (IId)

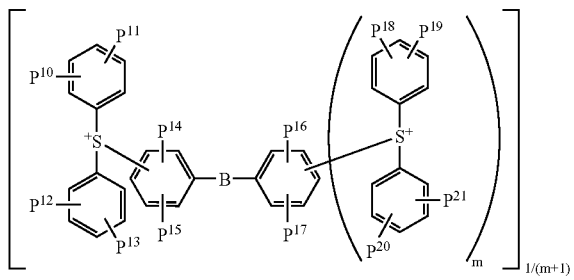
(IId)

wherein P¹⁰, P¹¹, P¹², P¹³, P¹⁴, P¹⁵, P¹⁶, P¹⁷, P¹⁸, P¹⁹, P²⁰ and P²¹ each independently represent hydrogen atom, hydroxyl group, alkyl group having 1 to 12 carbon atoms or alkoxy group having 1 to 12 carbon atoms, B represents sulfur atom or oxygen atom, and m represents 0 or 1.

<3> The salt according to <1>, wherein the A⁺ is a salt of the formula (IIe)

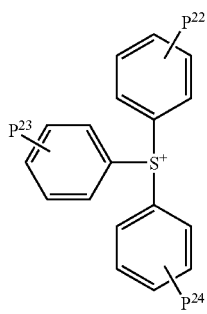
(IIe)

wherein P²², P²³ and P²⁴ each independently represent hydrogen atom or alkyl group having 1 to 4 atoms.

<4> The salt according to any of <1> to <3>, wherein X represents —OH group or —CH₂OH group, and n shows 1 or 2.

<5> The salt according to <1>, wherein the salt is the salt of the formula (IIIa) or (IIIb).

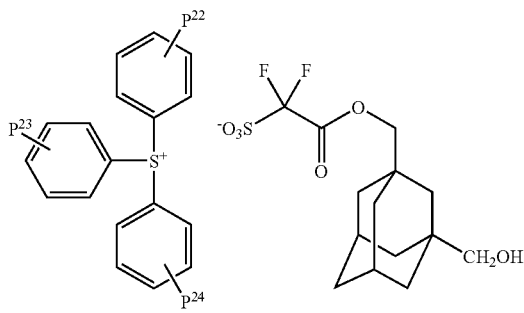
(IIIa)

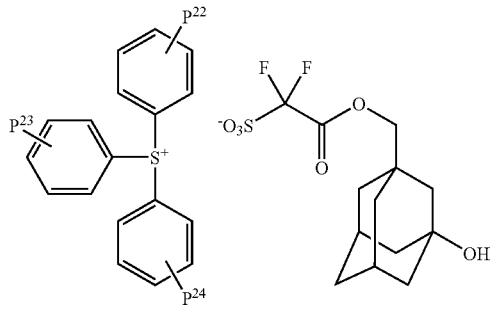
(IIIb)

wherein P²², P²³ and P²⁴ each independently represent hydrogen atom or alkyl group having 1 to 4 atoms.

<6> An ester of the formula (VI)

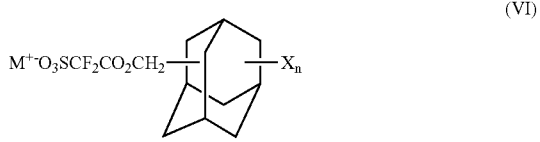
(VI)

wherein X and n have the same meaning as defined above, and M represents Li, Na, K or Ag.

<7> A process for producing an ester of the formula (VI), which comprises reacting an alcohol of the formula (IV)

(IV)

wherein X and n have the same meaning as defined above, with a carboxylic acid of the formula (V)

$$M^+{}^-O_3SCF_2COOH \tag{V}$$

wherein M has the same meaning as defined above.

<8> A process for producing a Salt (I), which comprises reacting an ester of the formula (VI) with an onium salt of the formula (VII)

$$A^+Z^- \tag{VII}$$

wherein A⁺ has the same meaning as defined above, and Z represents F⁻, Cl⁻, Br⁻, I⁻, BF₄⁻, AsF₆⁻, SbF₆⁻, PF₆⁻ or ClO₄⁻.

<9> A chemically amplified resist composition comprising Salt (I) and
a resin which contains a structural unit having an acid-labile group and which itself is insoluble or poorly soluble in an alkali aqueous solution but becomes soluble in an alkali aqueous solution by the action of an acid.

<10> The composition according to <9>, wherein the resin contains a structural unit derived from a monomer having a bulky and acid-labile group.

<11> The composition according to <10>, wherein the bulky and acid-labile group is 2-alkyl-2-adamantyl group or 1-(1-adamantyl)-1-alkylalkyl group.

<12> The composition according to <10>, wherein the monomer having bulky and acid-labile group is 2-alkyl-2-adamantyl (meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene- 2-carboxylate, 2-alkyl-2-adamantyl α-chloroacrylate or 1-(1-adamantyl)-1-alkylalkyl α-chloroacrylate.

<13> The composition according to any of <9> to <12>, wherein the composition further comprises a basic compound.

<14> The salt according to any of <9> to <13>, wherein A⁺ is at least one cation selected from the group consisting of the formulae (IIa), (IIb), (IIc) and (IId).

<15> The salt according to any of <9> to <13>, wherein A⁺ is a counter ion of the formula (IIe).

<16> The salt according to any of <9> to <15>, wherein X represents —OH group or —CH$_2$OH group, and n shows 1 or 2.

<17> The salt according to any of <9> to <13>, wherein the salt is the salt of the formula (IIIa) or (IIIb).

DESCRIPTION OF PREFERRED EMBODIMENTS

In Salt (I), X represents —OH group or —Y—OH group. Y represents a divalent saturated aliphatic hydrocarbon group having 1 to 6 carbon atoms. The aliphatic hydrocarbon group may be straight chained or branched.

Examples of Y include the following formulae (Y-1) to (Y-12), and the formulae (Y-1) and (Y-2) are preferred because of the easiness of the production.

—CH$_2$— (Y-1)

—CH$_2$—CH$_2$— (Y-2)

—CH$_2$—CH$_2$—CH$_2$— (Y-3)

—CH$_2$—CH$_2$—CH$_2$—CH$_2$— (Y-4)

—CH$_2$—CH$_2$—CH$_2$—CH$_2$—CH$_2$— (Y-5)

—CH$_2$—CH$_2$—CH$_2$—CH$_2$—CH$_2$—CH$_2$— (Y-6)

—CH$_2$—CH$_2$—
       |
       CH$_3$ (Y-7)

CH$_3$
      |
—C—
      |
     CH$_3$ (Y-8)

—CH$_2$—CH$_2$—CH—
              |
              CH$_3$ (Y-9)

—CH$_2$—CH$_2$—CH$_2$—
              |
              CH$_3$ (Y-10)

CH$_3$
         |
—CH$_2$—C—
         |
        CH$_3$ (Y-11)

CH$_3$
         |
—CH$_2$—C—CH$_2$—CH$_2$—
         |
        CH$_3$ (Y-12)

n, number of X in Salt (I), is 1 to 9, and 1 to 2 is preferred because of the easiness of production.

Specific examples of anion part in Salt (I) include the following anions.

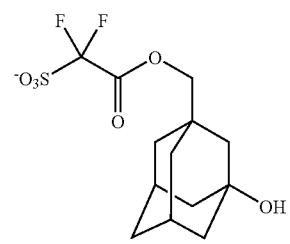

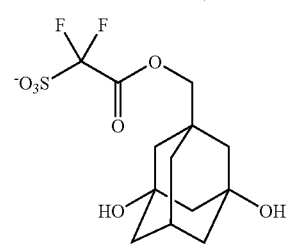

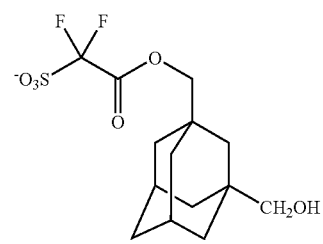

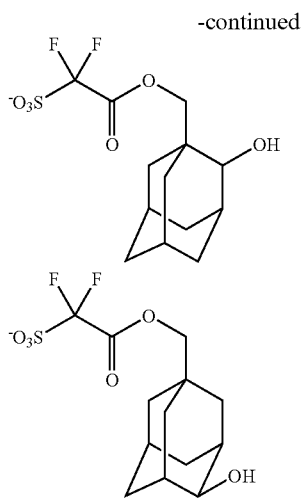

A⁺ in Salt (I) represents an organic counter ion. Examples thereof include the following cations of the formulae (IIa), (IIb), (IIc) and (IId).

In the cation of the formula (IIa), $P^1$, $P^2$ and $P^3$ each independently represent hydrogen atom, hydroxyl group, alkyl group having 1 to 12 carbon atoms or alkoxy group having 1 to 12 carbon atoms.

Examples of the alkyl group in the formula (IIa) include methyl group, ethyl group, propyl group, isopropyl group, butyl group, tert-butyl group, pentyl group, hexyl group, octyl group, 2-ethylhexyl group, and the like, and examples of the alkoxy group include methoxy group, ethoxy group, propoxy group, butoxy group, hexyloxy group, octyloxy group, 2-ethylhexyloxy group, and the like.

In the cation of the formula (IIa), the one of the formula (IIe) above is preferred for the easiness of production.

In the cation of the formula (IIb), $P^4$ and $P^5$ each independently represent hydrogen atom, hydroxyl group, alkyl group having 1 to 12 carbon atoms or alkoxy group having 1 to 12 carbon atoms. Examples of the alkyl group and alkoxy group include the same groups as mentioned in the formula (IIa) above.

In the cation of the formula (IIc), $P^6$ and $P^7$ each independently represent alkyl having 1 to 12 carbon atoms or cycloakyl having 3 to 12 carbon atoms, or $P^6$ and $P^7$ bond to form divalent acyclic hydrocarbon group having 3 to 12 carbon atoms which forms a ring together with the adjacent S⁺, and at least one —CH₂— in the divalent acyclic hydrocarbon may be substituted by —CO—, —O— or —S—.

$P^8$ represents hydrogen, $P^9$ represents alkyl having 1 to 12 carbon atoms, cycloalkyl having 3 to 12 carbon atoms or aromatic ring group optionally substituted, or $P^8$ and $P^9$ bond to form divalent acyclic hydrocarbon group which forms 2-oxocycloalkyl together with the adjacent —CHCO—, and at least one —CH₂— in the divalent acyclic hydrocarbon group may be substituted by —CO—, —O— or —S—.

In $P^6$, $P^7$ and $P^9$, specific examples of the alkyl group include methyl group, ethyl group, propyl group, isopropyl group, butyl group, tert-butyl group, pentyl group, hexyl group, and the like, and specific examples of the cycloalkyl group include cyclopropyl group, cyclobutyl group, cyclopentyl group, cyclohexyl group, cycloheptyl group, cyclodecyl group, and the like. Specific examples of the divalent acyclic hydrocarbon group having 3 to 12 carbon atoms formed by bonding $P^6$ and $P^7$ include methylene group, ethylene group, trimethylene group, tetramethylene group, pentamethylene group, and the like, and specific examples of the ring group formed by adjacent S⁺ and divalent acyclic hydrocarbon group by $P^6$ and $P^7$ include pentamethylenesulfonio group, tetramethylenesulfonio group, oxybisethylenesulfonio group, and the like. In $P^9$, specific examples of the aromatic ring group include phenyl, tolyl, xylyl, naphtyl and the like. Specific examples of the divalent acyclic hydrocarbon group formed by bonding $P^8$ and $P^9$ include methylene group, ethylene group, trimethylene group, tetramethylene group, pentamethylene group, and the like, and specific examples of the 2-oxocycloalkyl formed by bonding $P^8$ and $P^9$ together with the adjacent —CHCO— include 2-oxocyclohexyl, 2-oxocyclopentyl and the like.

In the cation of the formula (IId), $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen atom, hydroxyl group, alkyl group having 1 to 12 carbon atoms or alkoxy group having 1 to 12 carbon atom B represents sulfur atom or oxygen atom, and m represents 0 or 1. Examples of the alkyl group and alkoxy group include the same groups as mentioned in the formula (IIa) above.

Specific examples of the cation of the formula (IIa) include the following:

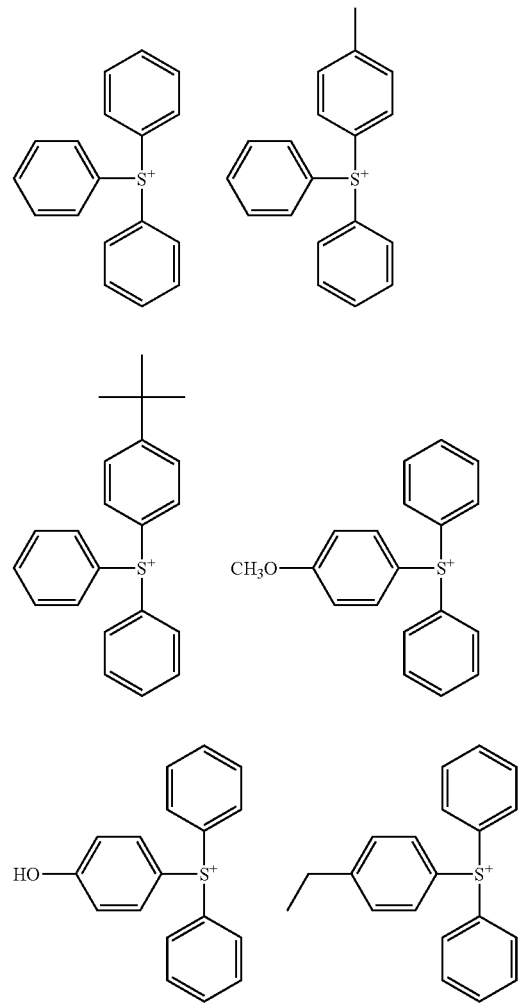

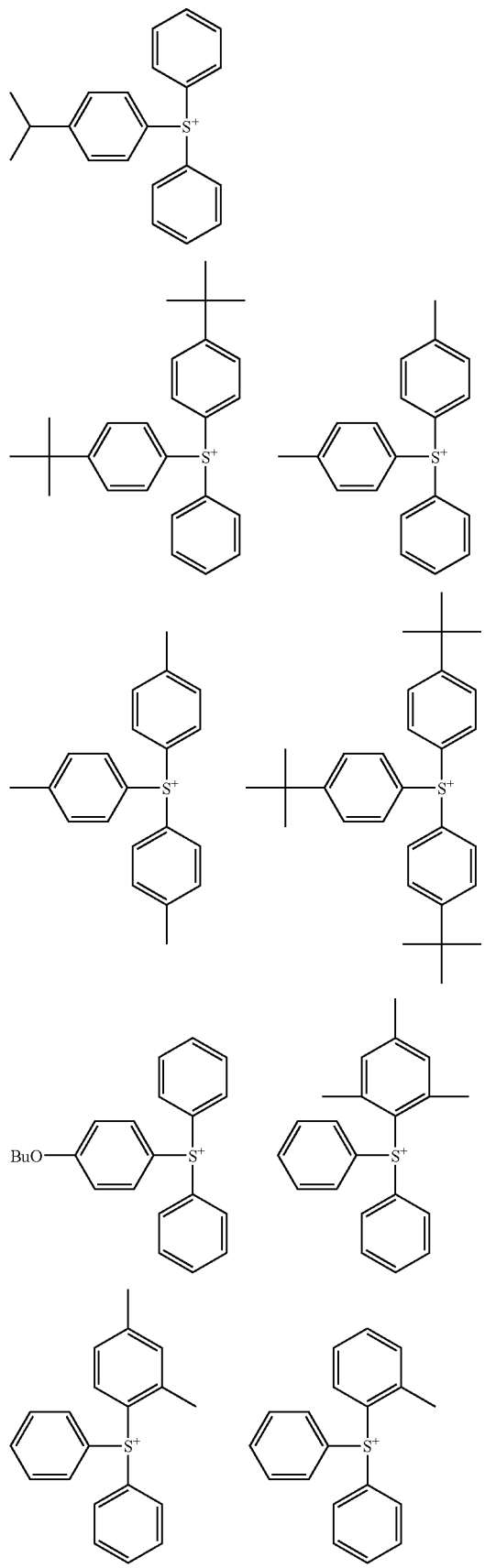
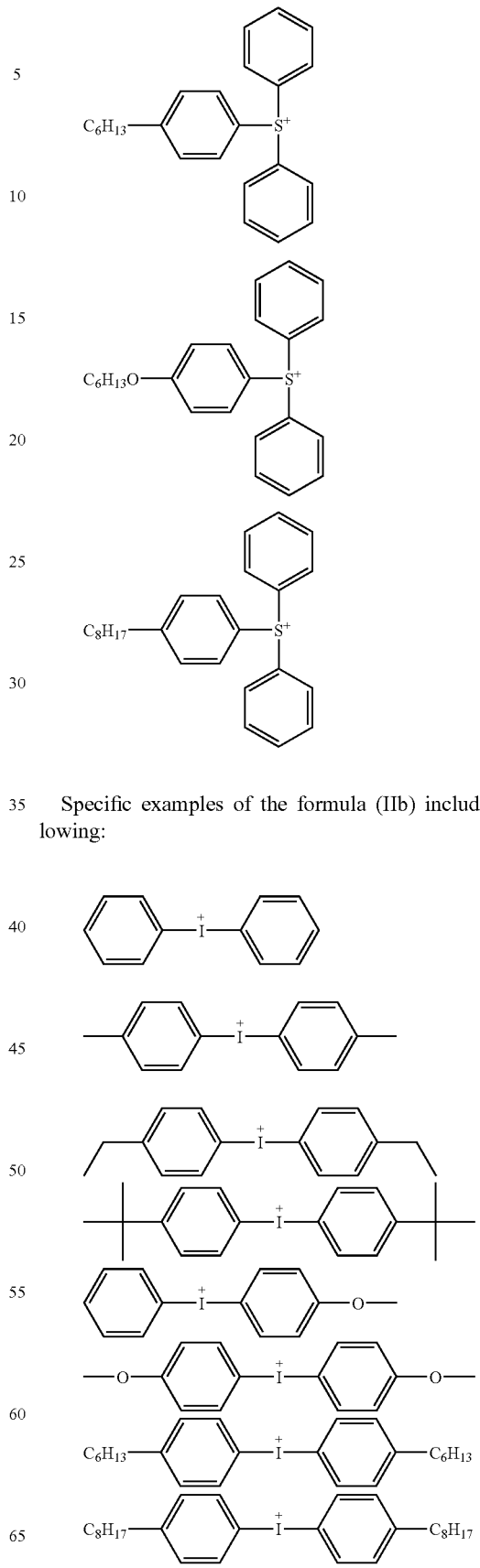
Specific examples of the formula (IIb) include the following:

Specific examples of the formula (IIc) include the following:
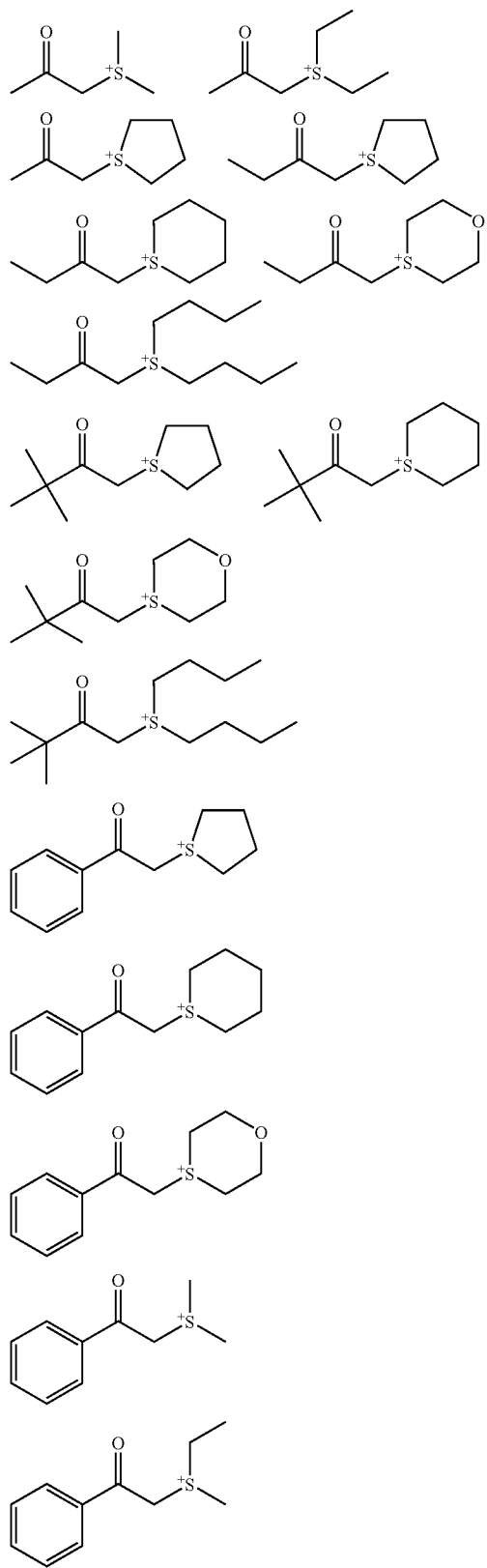
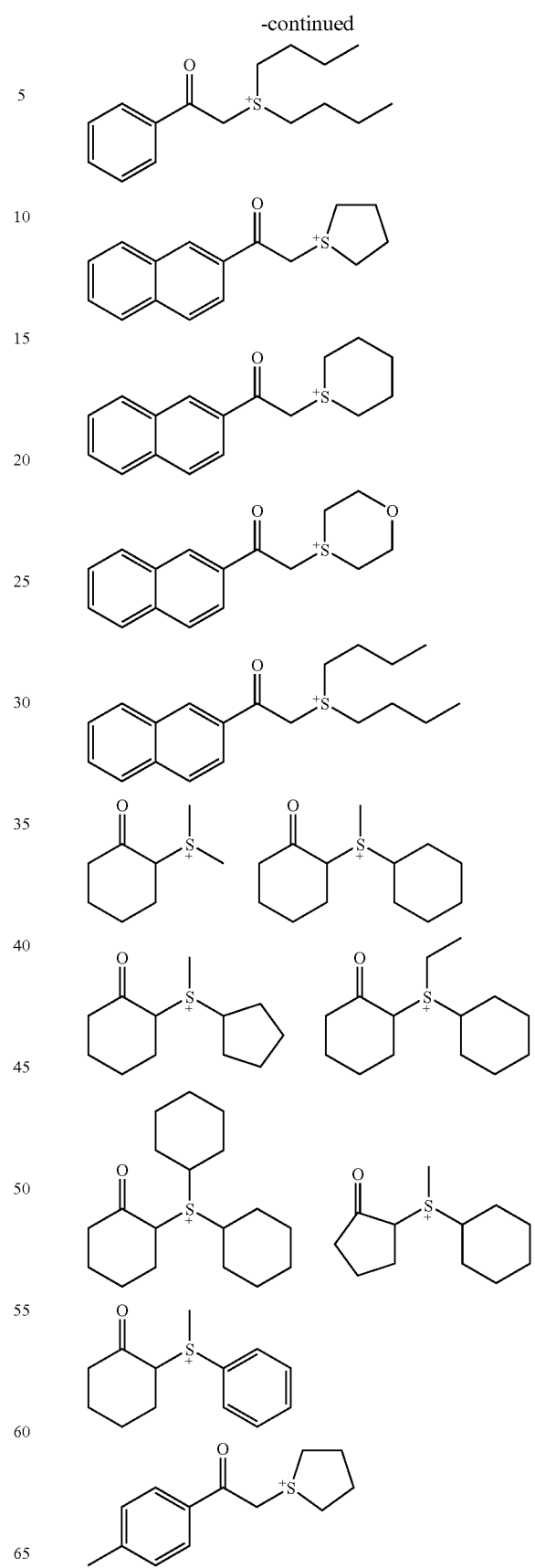

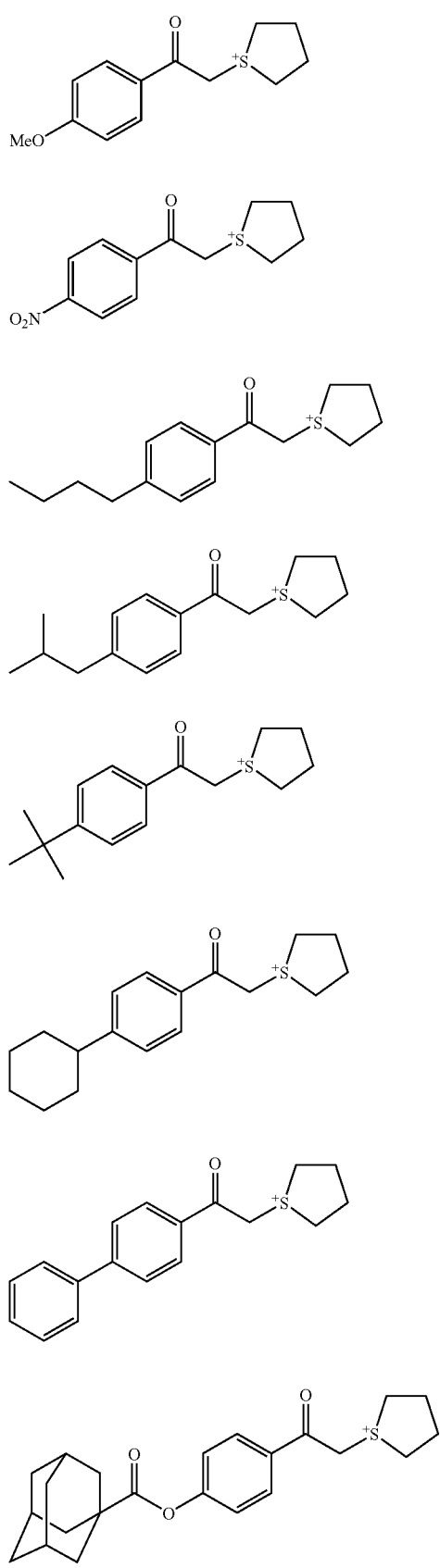
Specific examples of the cation of the formula (IId) include the following:
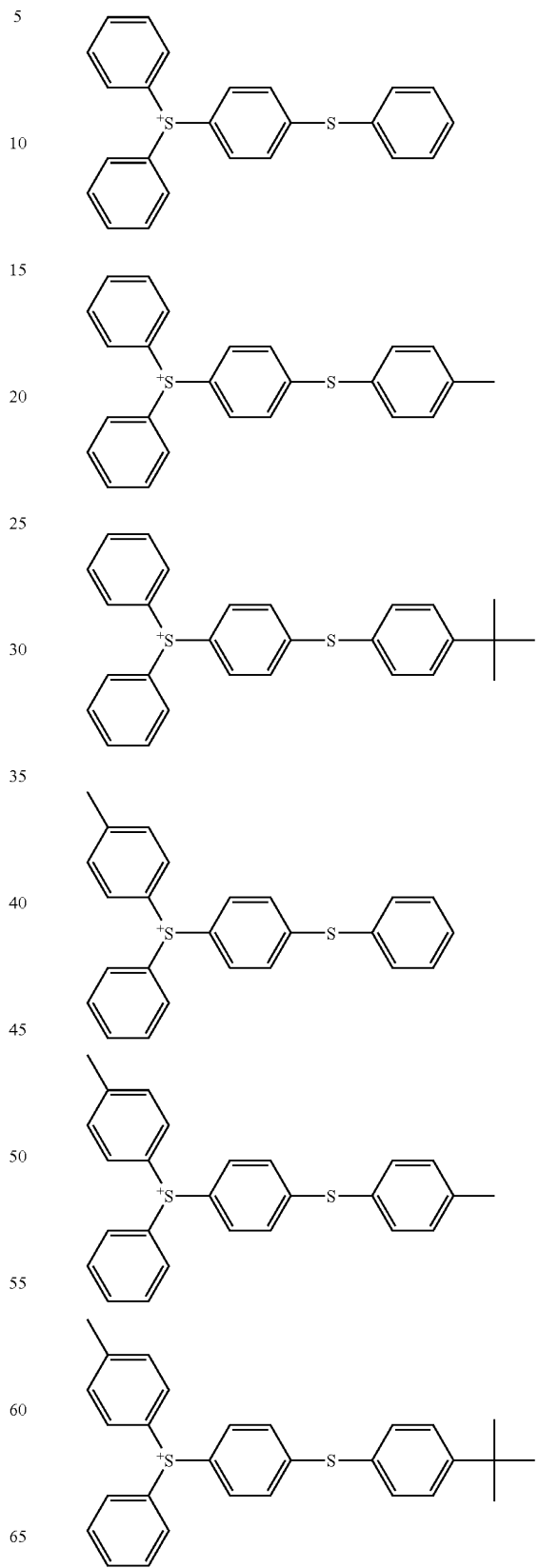

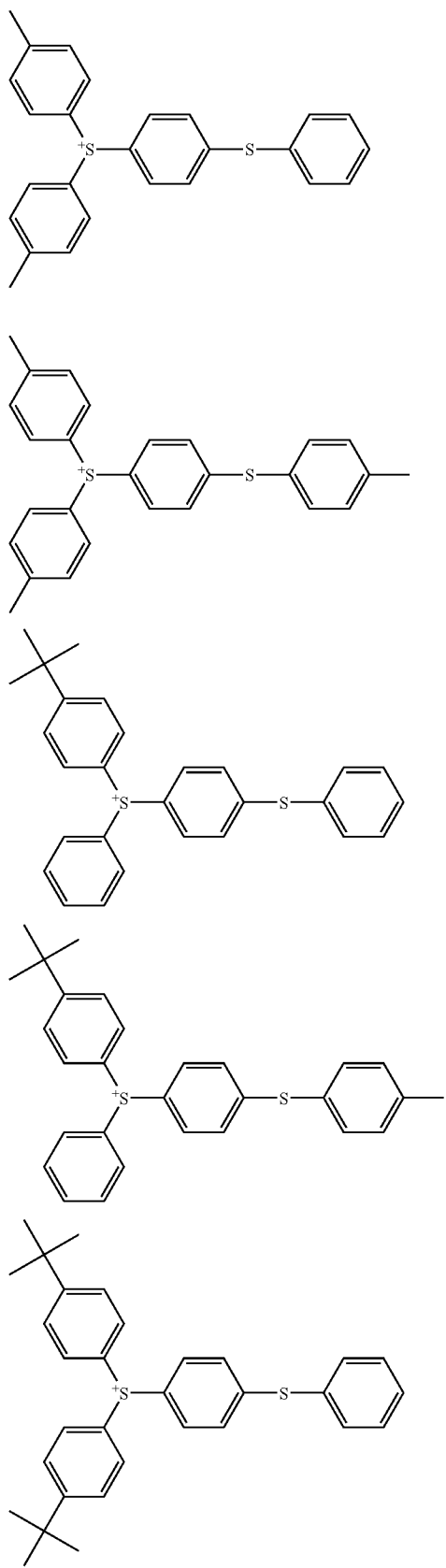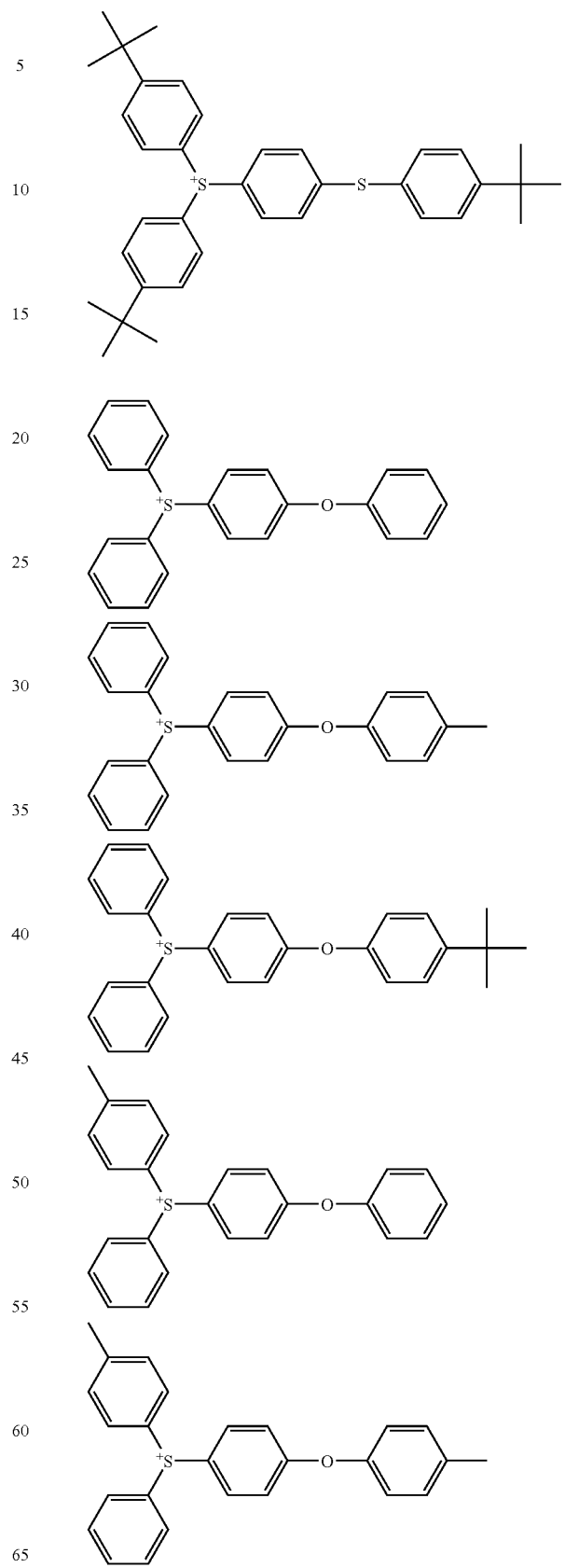

-continued
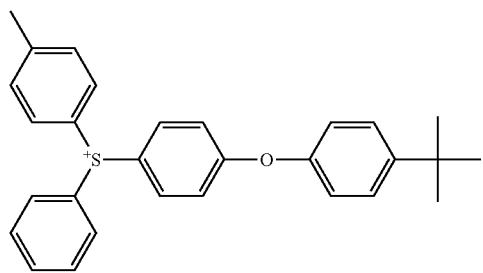
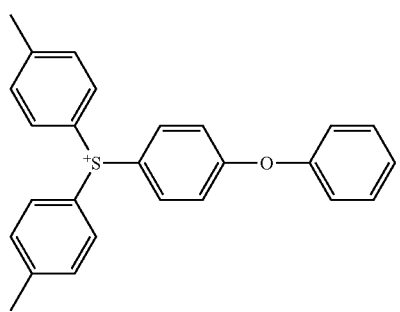
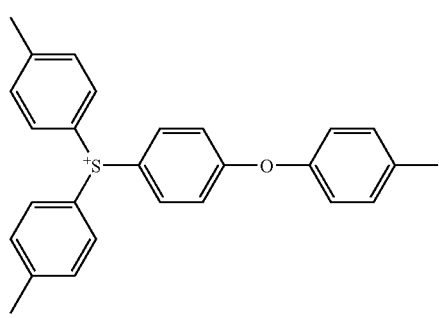
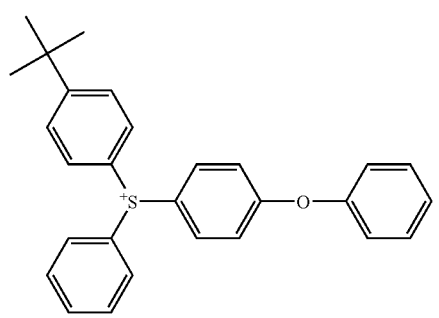
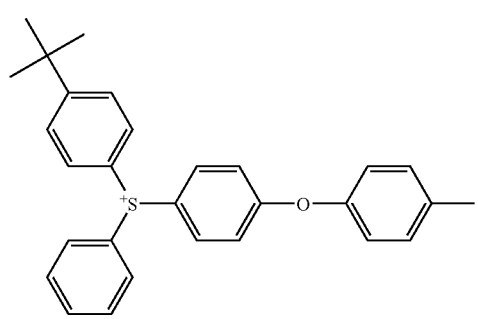
-continued
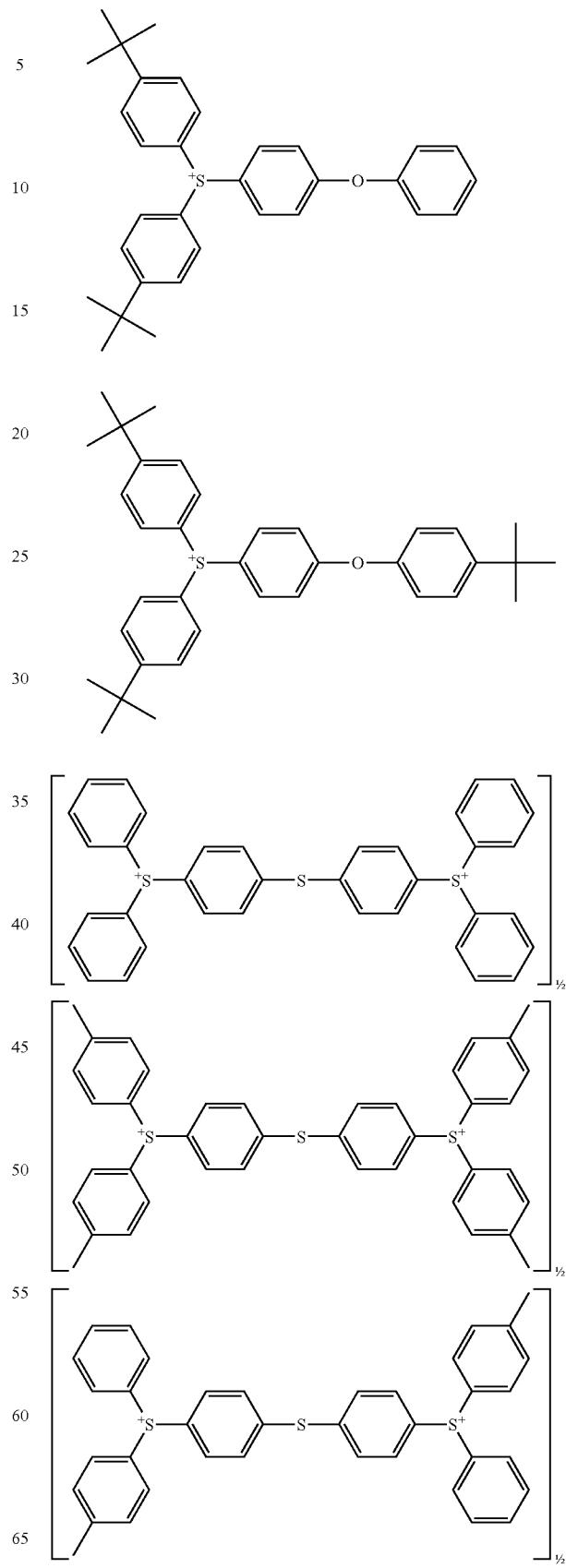

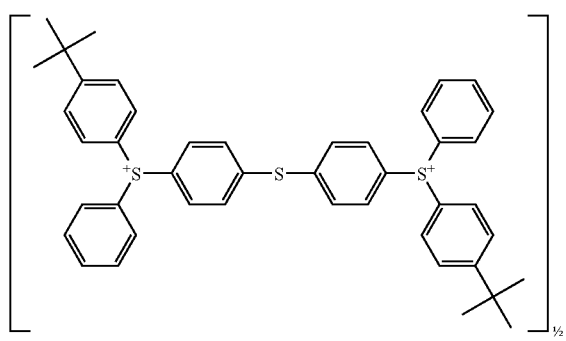
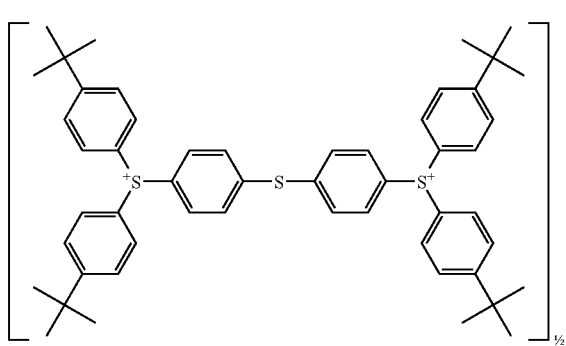
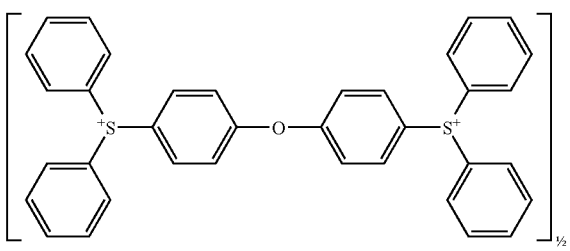
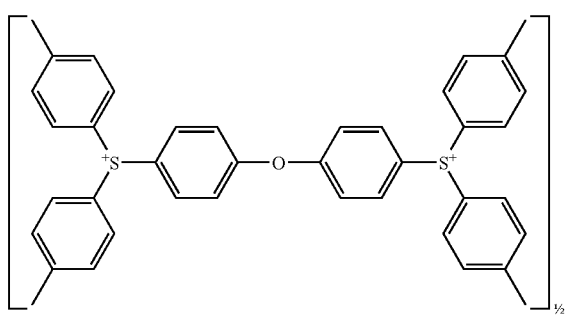
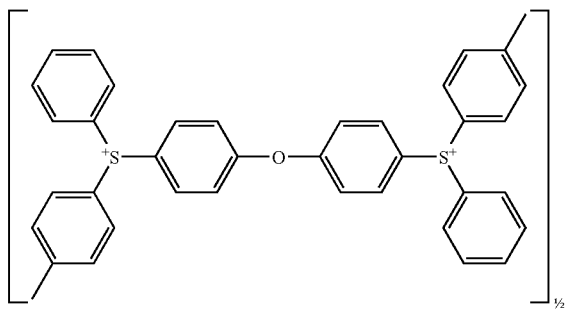
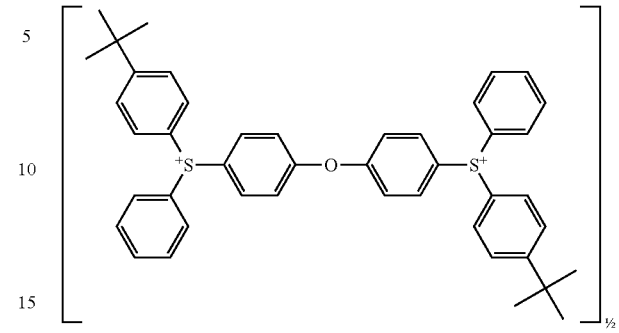
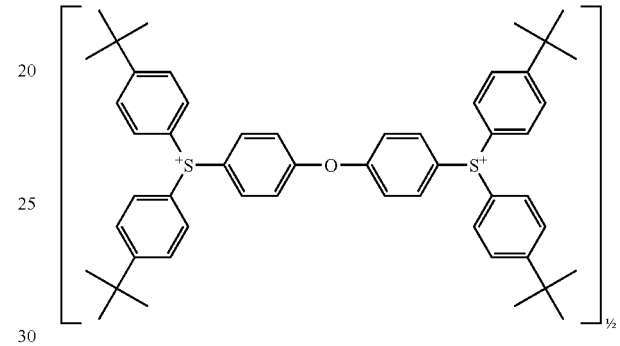
As Salt (I), the salts of the formulae (IIIa) and (IIIb) are preferred, and the salts of the following formulae (IIIa') and (IIIb') are preferred, for the excellent resolution and pattern profile.
(IIIa')
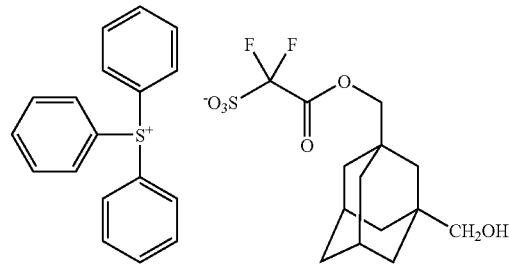
(IIIb')
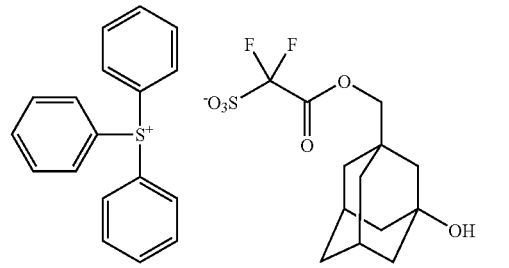
Examples of a process for production of Salt (I) include a process comprising reacting an ester of the formula (VI) with an onium salt of the formula (VII), in an inert solvent such as acetonitrile, water, methanol, chloroform and dichloromethane at a temperature of 0 to 150° C., preferably of 0 to 100° C.

The amount of the onium salt of the formula (VII) is usually 0.5 to 2 mol per 1 mol of the ester of the formula (VI). Salt (I) obtained can be taken out by recrystallization when it is in crystal form or by extraction by solvents and concentration when it is in oil form.

Examples of a process for production of the ester of the formula (VI) include a process reacting an alcohol of the formula (IV) with a carboxylic acid of the formula (V).

The esterification reaction can generally be carried out by materials in an aprotic solvent such as dichloroethane, toluene, ethylbenzene, monochlorobenzene, acetonitrile, N,N-dimethylformamide, and the like, at 20 to 200° C., preferably 50 to 150° C. In the esterification reaction, an acid catalyst or a dehydrating agent is usually added, and examples of the acid catalyst include organic acids such as p-toluenesulfonic acid, inorganic acids such as sulfuric acid, and the like. Examples of the dehydrating agent include 1,1'-carbonyldiimidazole, N,N'-dicyclohexylcarbodiimide, and the like.

The esterification may preferably be carried out with dehydration, for example, by Dean and Stark method as the reaction time tends to be shortened.

The amount of the carboxylic acid of the formula (V) is usually 0.2 to 3 mol, preferably 0.5 to 2 mol per 1 mol of the alcohol of the formula (IV). The amount of the acid catalyst may be catalytic amount or the amount equivalent to solvent, and is usually 0.001 to 5 mol per 1 mol of the alcohol of the formula (IV). The amount of the dehydrating agent is usually 0.2 to 5 mol preferably 0.5 to 3 mol per 1 mol of the alcohol of the formula (IV).

The present chemically amplified resist composition comprises Salt (I) and a resin which contains a structural unit having an acid-labile group and which itself is insoluble or poorly soluble in an alkali aqueous solution but becomes soluble in an alkali aqueous solution by the action of an acid.

Salt (I) is usually used as an acid generator, and the acid generated by irradiation to Salt (I) catalytically acts against acid-labile groups in a resin, cleaves the acid-labile-group, and the resin becomes soluble in an alkali aqueous solution. Such a composition is suitable for chemically amplified positive resist composition.

The resin used for the present composition contains a structural unit having an acid-labile group and which itself is insoluble or poorly soluble in an alkali aqueous solution, but acid-labile group cleave by an acid. The resin after the cleavage contains carboxylic acid residue and as a result, the resin becomes soluble in an alkali aqueous solution.

In the present specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, and alicyclic ester group in which a cation atom adjacent to the oxygen atom is quaternary carbon atom, and the like, a lactone ring group in which a carbon atom adjacent to the oxygen atom is quaternary carbon atom, and the like.

The "quaternary carbon atom" means a "carbon atom joined to four substituents other than hydrogen atom". As the acid-labile group, a group having a quaternary carbon atom joined to three carbon atoms and a OR', wherein R' represents alkyl group.

Examples of the acid-labile group include alkyl ester group in which a carbon atom adjacent to the oxygen atom is quaternary carbon atom such as tert-butyl ester group; acetal type ester group such as methoxymethyl ester group, ethoxymethyl ester group, 1-ethoxyethyl ester group, 1-isobutoxyethyl ester group, 1-isopropoxyethyl ester group, 1-ethoxypropoxy ester group, 1-(2-methoxyethoxy) ethyl ester, 1-(2-acetoxyethoxy)ethyl ester group, 1-[2-(1-adamantyloxy)ethoxy]ethyl ester group, 1-[2-(1-adamantanecarbonylyloxy)ethoxy]ethyl ester group, tetrahydro-2-furyl ester and tetrahydro-2-pyranyl ester group; alicyclic ester group in which a carbon atom adjacent to the oxygen atom is quaternary carbon atom, such as isobornyl ester group, 1-alkylcycloalkyl ester group, 2-alkyl-2-adamantyl ester group, 1-(1-adamantyl)-1-alkylalkyl ester group, and the like.

Examples of structures including the ester group include ester of (meth)acrylic acid structure, ester of norbornenecarboxylic acid structure, ester of tricyclodecenecarboxylic acid structure, tetracyclodecenecarboxylic acid structure, and the like. At least one hydrogen atom in the adamantyl group above may be substituted by hydroxyl group.

The resin used for the present composition can be obtained by addition polymerization of monomer(s) having an add-labile group and olefinic double bond.

Among the monomers, it is preferable to use those having a bulky group such as alicyclic group (e.g. 2-alkyl-2-adamantyl and 1-(1-adamantyl-1-alkylalkyl), as the group dissociated by the action of an acid, since excellent resolution is obtained when used in the present composition.

Examples of such monomer containing a bulky group include 2-allyl-2-adamantyl (meth)acrylate, 1-(1-adamantyl)-1-alkylalkyl(meth)acrylate, 2-alkyl-2-adamantyl 5-norbornene-2-carboxylate, 1-(1-adamantyl)-1-alkylalkyl-5-norbornene-2-carboxylate, 2-alkyl-2-adamantyl α-chloroacrylate, 1-(1-adamantyl)-1-alkylalkyl α-chloroacrylate and the like.

Particularly when 2-alkyl-2-adamantyl(meth)acrylate or 2-alkyl-2-adamantyl α-chloroacrylate is used as the monomer for the resin component in the present composition, resist composition having excellent resolution tend to be obtained. Typical examples of such 2-alkyl-2-adamantyl (meth)acrylate and 2-alkyl-2-adamantyl α-chloroacrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate, 2-ethyl-2-adamantyl α-chloroacrylate and the like. When particularly 2-ethyl-2-adamantyl(meth)acrylate or 2-isopropyl-2-adamantyl (meth)acrylate is used for the present composition, composition having excellent sensitivity and heat resistance tends to be obtained in the present invention, two or more kind of monomers having group dissociated by the action of an acid may be used together, if necessary.

2-Alkyl-2-adamantyl(meth)acrylate can usually be produced by reacting 2-alkyl-2-adamantanol or metal salt thereof with an acrylic halide or methacrylic halide.

The resin used for the present composition can also contain, in addition to the above-mentioned structural units having an acid-labile group, other structural unit derived from acid-stable monomer. Herein, the "structural unit derived from acid-stable monomer" means "a structural unit not dissociated by an acid generated from Salt (I)".

Examples of such other structural units which can be contained include structural units derived from monomers having a free carboxyl group such as acrylic acid and methacrylic acid, structural units derived from aliphatic unsaturated dicarboxylic anhydrides such as maleic anhydride and itaconic anhydride, structural units derived from 2-norbornene, structural units derived from (meth)acrylonitrile, structural units derived from alkyl(meth)acrylate in which a carbon atom adjacent to oxygen atom is secondary or tertiary carbon atom, structural units derived from 1-adamantyl(meth)acrylate, structural units derived from styrenes such as p- or m-hydroxystyrene, structural units derived from (meth)acryloyoxy-γ-butyrolactone having a lactone ring optionally substituted by alkyl, and the like. Herein, 1-adamantyl ester group is a acid-stable group though the carbon atom adjacent to oxygen atom is a quaternary carbon atom, and at least one hydrogen atom on 1-adamantyl ester group may be substituted by hydroxy group.

Specific examples of structural unit derived from acid-stable monomer include a structural unit derived from 3-hydroxyl-1-adamantyl(meth)acrylate, a structural unit derived from 3,5-dihydroxy-1-adamantyl(meth)acrylate, a structural unit derived from α-(meth)acryloyloxy-γ-butyrolactone, a structural unit derived from β-(meth)acryloyloxy-γ-butyrolactone, a structural unit of the following formula (a), a structural unit derived from the following formula (b), a structural unit derived from alicyclic compound having olefinic double bond such as a structural unit of the following formula (c), a structural unit derived from aliphatic unsaturated dicarboxylic anhydride such as a structural unit of the formula (d), a structural unit of the formula (e), and the like.

Particularly, to contain, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-hydroxy-1-adamantyl(meth)acrylate, a structural unit of the following formula (a) and a structural unit of the following formula (b), in the resin in the present composition, is preferable from the standpoint of the adhesiveness of resist to a substrate and resolution of resist.

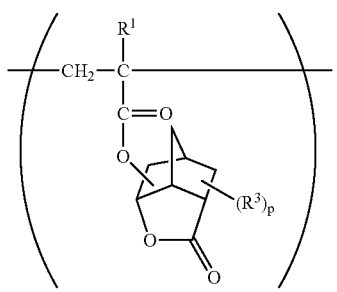

(a)

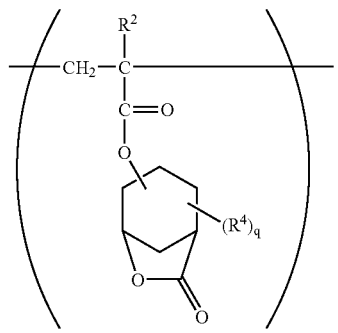

(b)

In the formulae (a) and (b), $R^1$ and $R^2$ each independently represent hydrogen atom, methyl group or trifluoromethyl group and $R^3$ and $R^4$ each independently represent methyl group, trifluoromethyl group or halogen atom and p and q each independently represent an integer of 0 to 3. When p represents 2 or 3, each of the $R^3$ may be the same or different and when q represents 2 or 3, each of the $R^4$ may be the same or different.

3-Hydroxy-1-adamantyl(meth)acrylate and 3,5-dihydroxy-1-adamantyl(meth)acrylate can be produced, for example, by reacting corresponding hydroxyadamantane with (meth)acrylic acid or its acid halide, and they are also commercially available.

Further, (meth)acryloyloxy-γ-butyrolactone having a lactone ring optionally substituted by alkyl can be produced by reacting corresponding α- or β-bromo-γ-butyrolactone with acrylic acid or methacrylic acid, or reacting corresponding α- or β-hydroxy-γ-butyrolactone with acrylic halide or methacrylic halide.

As monomers to give structural units of the formulae (a) and (b), specifically listed are, for example, (meth)acrylates of alicyclic lactones having hydroxyl described below, and mixtures thereof, and the like. These esters can be produced, for example, by reacting corresponding alicyclic lactone having hydroxyl with (meth)acrylic acids, and the production method thereof is described in, for example, JP2000-26446-A.

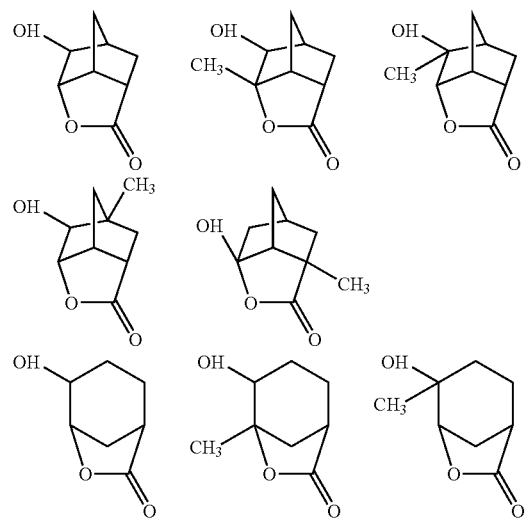

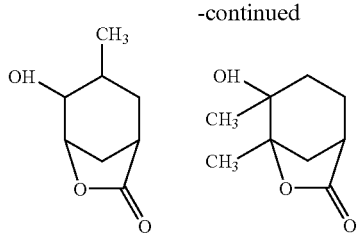

Examples of the (meth)acryloyloxy-γ-butyrolactone having a lactone ring optionally substituted by alkyl include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, β-methacryloyloxy-α-methyl-γ-butyrolactone and the like.

In the case of KrF lithography, even in the case of using a structure unit derived from hydroxystyrene such as p- and m-hydroxystyrene, as one of the resin components, resist composition having sufficient transparency can be obtained. For obtaining such copolymerization resins, the corresponding (meth)acrylic ester monomer can be radical-polymerized with acetoxystyrene and styrene, and then the acetoxy group in the structure unit derived from acetoxystyrene can be de-acetylated with an acid.

The resin changing a structural unit derived from 2-norbornene shows strong structure because alicyclic group is directly present on its main chain and shows a property that dry etching resistance is excellent. The structural unit derived from 2-norbornene can be introduced into the main in by radical polymerization using for example, in addition to corresponding 2-norbornene, aliphatic unsaturated dicarboxylic anhydrides such as maleic anhydride and itaconic anhydride together. The structural unit derived from 2-norbornene is formed by opening of its double bond, and can be represented by the formula (c). The structural unit derived from maleic anhydride and the structural unit derived from itaconic anhydride which are the structural unit derived from aliphatic unsaturated dicarboxylic anhydrides are formed by opening of their double bonds, and can be represented by the formula (d) and the formula (e), respectively.

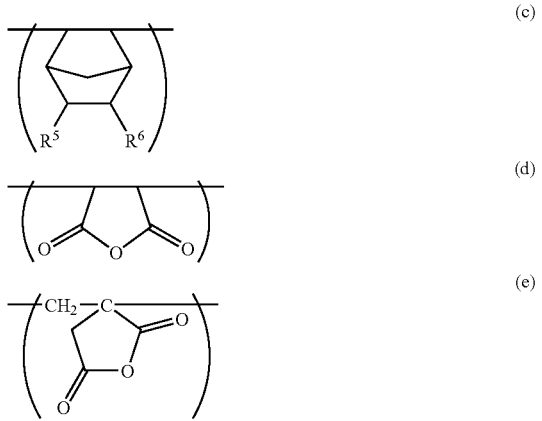

Here, $R^5$ and $R^6$ in the formula (c) each independently represent hydrogen, alkyl having 1 to 3 carbon atoms, hydroxyalkyl having 1 to 3 carbon atoms, carboxyl cyano or —COOU group in which U represents alcohol residue, or $R^5$ and $R^6$ can bond together to form a carboxylic anhydride residue represented by —C(=O)OC(=O)—.

In $R^5$ and $R^6$, examples of the alkyl include methyl, ethyl, propyl and isopropyl, specific examples of hydroxyalkyl include hydroxymethyl, 2-hydroxyethyl and the like.

In $R^5$ and $R^6$, —COOU group is an ester formed from carboxy and as the alcohol residue corresponding to U, for example, optionally substituted alkyls having about 1 to 8 carbon atoms, 2-oxooxolan-3- or 4-yl and the like are listed, and as the substituent on the alkyl, hydroxyl, alicyclic hydrocarbon residues and the like are listed.

Specific examples of the monomer used to give the structural unit represented by the formula (c) may include the followings;
  2-norbornene,
  2-hydroxy-5-norbornene,
  5-norbornen-2-carboxylic acid,
  methyl 5-norbornen-2-carboxylate,
  2-hydroxyethyl 5-norbornene-2-carboxylate,
  5-norbornen-2-methanol,
  5-norbornen-2,3-dicarboxylic acid anhydride, and the like.

When U in —COOU is acid-labile group, the structural unit of the formula (c) is a structural unit having acid-labile group even if it has norbornene structure. Examples of monomers giving structural unit having acid-labile group include t-butyl 5-norbornen-2-carboxylic, 1-cyclohexyl-1-methylethyl 5-norbornen-2-carboxylate, 1-methylcyclohexyl-5-norbornen-2-carboxylate, 2-methyl-2-adamantyl 5-norbornen-2-carboxylate, 2-ethyl-2-adamantyl 5-norbornen-2-carboxylate, 1-(4-methylcyclohexyl)-1-methylethyl 5-norbornen-2-carboxylate, 1-(4-hydroxylcyclohexyl)-1-methylethyl 5-norbornen-carboxylate, 1-methyl-1-(4-oxocyclohexyl)ethyl 5-norbornen-2-carboxylate, 1-(1-adamantyl)-1-methylethyl 5-norbornen-2-carboxylate, and the like.

The resin used in the present composition preferably contains structural unit(s) having an acid-labile group generally in a ratio of 10 to 80% by mol in all structural units of the resin though the ratio varies depending on the kind of radiation for patterning exposure, the kind of an acid-labile group, and the like.

When the structural units particularly derived from 2-alkyl-2-adamantyl(meth)acrylate or 1-(1-adamantyl)-1-alkylalkyl(meth)acrylate are used as the acid-labile group, it is advantageous that the ratio of the structural units is 15% by mol or more in all structural units of the resin.

When, in addition to structural units having an acid-labile group, other structural units having acid-stable group are contained, it is preferable that the sum of these structural units is in the range of 20 to 90% by mol based on all structural units of the resin.

When alicyclic compound having olefinic double bond and aliphatic unsaturated dicarboxylic anhydride are used as copolymerization monomer, it is preferable to use them in excess amount in view of a tendency that these are not easily polymerized.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen containing organic compounds include the ones represented by the following formulae:

[3]

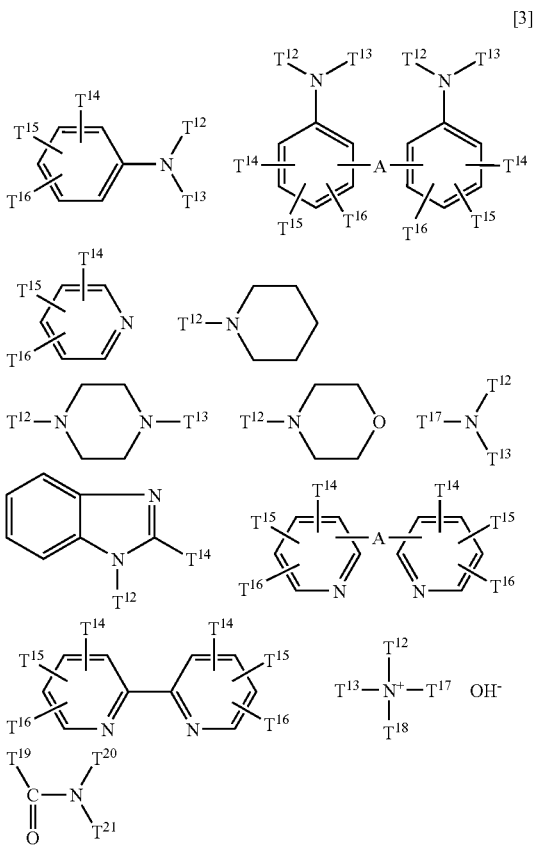

In the formulas, $T^{12}$ and $T^{13}$ each independently represent a hydrogen atom, an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with hydroxyl group, amino group, or alkoxy group having 1 to 6 carbon atoms. At least one hydrogen atom on the amino group may each independently be substituted with alkyl group having 1 to 4 carbon atoms.

$T^{14}$, $T^{15}$ and $T^{16}$ each independently represent a hydrogen atom, an alkyl group, a cycloalkyl group, an aryl group or an alkoxy group. The alkyl group preferably has about 1 to 6 carbon atoms, the cycloalkyl group preferably has about 5 to 10 carbon atoms, the aryl group preferably has about 6 to 10 carbon atoms, and the alkoxy group preferably has about 1 to 6 carbon atoms. Furthermore, at least one hydrogen atom on the alkyl group, cycloalkyl group, aryl group or alkoxy group may each independently be substituted with hydroxyl group, amino group, or alkoxy group having 1 to 6 carbon atoms. At least one hydrogen atom on the amino group may be substituted with alkyl group having 1 to 4 carbon atoms.

$T^{17}$ represents an alkyl group or a cycloalkyl group. The alkyl group preferably has about 1 to 6 carbon atoms, and the cycloalkyl group preferably has about 5 to 10 carbon atoms. Furthermore, at least one hydrogen atom on the alkyl group or cycloalkyl group may each independently be substituted with hydroxyl group, amino group, or alkoxy group having 1 to 6 carbon atoms. At least one hydrogen atom on the amino group may be substituted with alkyl group having 1 to 4 carbon atoms.

In the formulas, $T^{18}$ represents an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with a hydroxyl group, an amino group, or an alkoxy group having 1 to 6 carbon atoms. At least one hydrogen atom on the amino group may each independently be substituted with alkyl group having 1 to 4 carbon atoms.

However, none of $T^{12}$ and $T^{13}$ in the compound represented by the above formula [3] is a hydrogen atom.

A represents alkylene group, carbonyl group, imino group, sulfide group or disulfide group. The alkylene group preferably has about 2 to 6 carbon atoms.

Moreover, among $T^{12}$-$T^{18}$, in regard to those which can be straight-chained or branched, either of these may be permitted.

$T^{19}$, $T^{20}$ and $T^{21}$ each independently represent a hydrogen atom, an alkyl group having 1 to 6 carbon atoms, an aminoalkyl group having 1 to 6 carbon atoms, a hydroxyalkyl group having 1 to 6 carbon atoms or a substituted or unsubstituted aryl group having 6 to 20 carbon atoms, or $T^{19}$ and $T^{20}$ bond to form an alkylene group which forms a lactam ring together with adjacent —CO—N—.

Examples of such compounds include hexylamine, heptylamine, octylamine, nonylamine, decylamine, aniline, 2-, 3- or 4-methylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-isopropylaniline, pyridine, 4-methylpyridine, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl)trimethylammonium hydroxide (so-called "choline"), N-methylpyrrolidone, and the like.

Furthermore, hindered amine compounds having piperidine skeleton as disclosed in JP-A-H11-52575 can be used as quencher.

It is preferable that the present composition contains resin component in an amount of about 80 to 99.9% by weight and Salt (I) in an amount of 0.1 to 20% by weight on the total amount of the resin component and Salt (I).

When basic compound is used as a quencher, the basic compound is contained preferably in an amount of about 0.01 to 1 part by weight per 100 parts by weight of sum of resin component and Salt (I).

The present composition can contain if necessary, various additives in small amount such as a sensitizer, solution suppressing agent, other polymers, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. In the present invention, the total solid content means total content exclusive of solvents.

Examples thereof include glycol ether esters such as ethyl Cellosolve acetate, methyl Cellosolve acetate and propylene glycol monomethyl ether acetate; glycol ethers such as propylene glycol monomethyl ether, di(ethylene glycol) dimethyl ether, esters such as ethyl lactate, butyl lactate, amyl lactate and ethyl pyruvate and the like; ketones such as acetone, methyl isobutyl ketone, 2-heptanone and cyclohexanone; cyclic esters such as γ-butyrolactone, and the like. These solvents can be used each alone or in combination of two or more.

A resist film applied onto the substrate and then dried is subjected to exposure for patterning then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by way of examples, which are not construed to limit the scope of the present invention. The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns): TSKgel Multipore HXL-M, Solvent: Tetrahydrofuran, manufactured by TOSOH CORPORATION] using styrene as a standard reference material. Structures of compounds were determined by NMR (GX-270 Type, or EX-270 Type, manufactured by JEOL LTD) and mass spectrometry (Liquid Chromatography: 1100 Type, manufactured by AGILENT TECHNOLOGIES LTD, Mass Spectometry: LC/MSD Type or LC/MSD TOF Type, manufactured by AGILENT TECHNOLOGIES LTD.).

EXAMPLE 1

(Synthesis of triphenylsulfonium 1-((3-hydroxymethyladamantyl)methoxycarbonyl)-difluoromethanesulfonate)

(1) 230 Parts of 30% aqueous sodium hydroxide solution was added into a mixture of 100 parts of methyl difluoro (fluorosulfonyl)acetate and 250 parts of ion-exchanged water in a ice bath. The added mix was heated and refluxed at 100° C. for 3 hours. After cooling, the cooled mixture was neutralized with 88 parts of conc. hydrochloric acid and concentrated to obtain 164.8 parts of sodium difluorosulfoacetate (containing inorganic salt, purity: 62.6%).

(2) 2.5 Parts of sodium difluorosulfoacetate (purity 62.6%), 3.1 parts of 1,3-adamantanedimethanol and 62 parts of dichloroethane were charged in a vessel, 1.5 parts of p-toluenesulfonic acid (p-TsOH) was added thereto, and the mixture was refluxed for 5 hours. After concentrating the mixture to eliminate dichloroethane, 100 parts of acetonitrile was added thereto, and the added mixture was stirred. The stirred mixture was filtrated and concentrated to obtain 3.5 parts of sodium salt of 3-hydroxymethyl-1-adamantylmethyl difluorosulfoacetate.

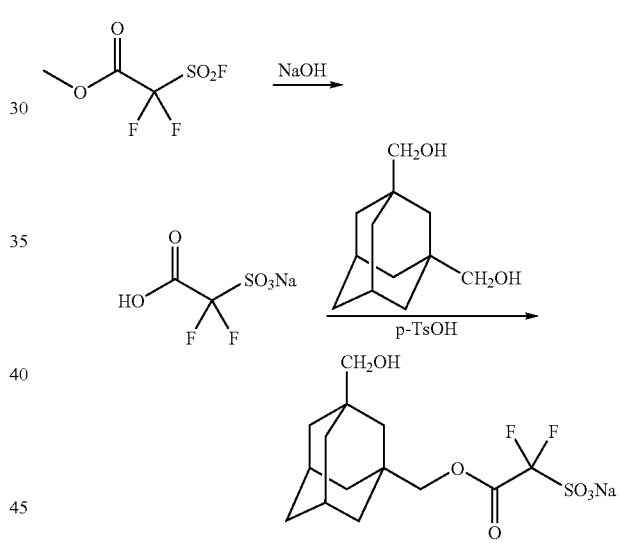

$^1$H-NMR data of so salt of 3-hydroxymethyl-1-adamantyl-methyl difluorosulfoacetate (dimethylsulfoxide-$d_6$, Internal Standard: tetramethylsilane): d(ppm) 1.22-153(m, 12H); 1.98(s, 2H); 2.98(d, 2H); 3.82(s, 2H); 4.35(t, 1H)

(3) 3.5 Parts of sodium salt of 3-hydroxymethyl-1-adamantylmethyl difluorosulfoacetate obtained in (2) was dissolved in 35 parts of acetonitrile. 2.8 parts of triphenylsulfonium chloride and 28 par of ion-exchanged water were added to the solution. After stirred for 15 hours, the stirred mixture was concentrated and extracted with 100 parts of chloroform twice. The organic layers were mixed and washed with ion-exchanged water. The obtained of organic layer was concentrated. The concentrate was washed with each of 50 parts of tert-butyl methyl ether and 50 parts of ethyl acetate and each of the solvent was decanted. Then, 200 parts of ethyl acetate was added to the washed concentrate, the mixture was stirred to obtain a solution, and the solution was filtrated. The filtrated solution was concentrated to obtain 0.5 part of triphenylsulfonium 1((3-hydroxymethyladamantyl)methoxycarbonyl)-difluoromethanesulfonate in the form of pale yellow oil, which is called as acid generator B1.

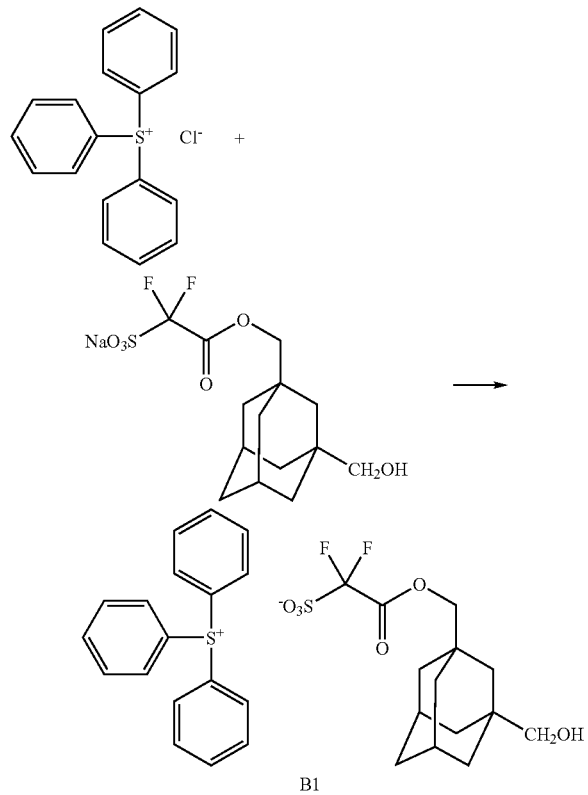

B1

$^1$H-NMR data of B1 (dimethylsulfoxide-d$_6$, Internal Standard: tetramethylsilane): d(ppm) 1.22-1.53(m, 12H); 1.98(S, 2H); 2.98(d, 2H); 3.82(s, 2H); 4.35(t, 1H); 7.74-7.88(m, 15H) MS (ESI(+) Spectrum): M+263.0 (C$_{18}$H$_{15}$S$^+$=263.09) MS (ESI(−) Spectrums): M−353.0 (C$_{14}$H$_{19}$F$_2$O$_6$S$^-$=353.09)

EXAMPLE 2

(Synthesis of triphenylsulfonium 1-((3-hydroxyadamantyl)methoxycarbonyl)difluoromethanesulfonate (1) 230 Parts of 30% aqueous sodium hydroxide solution was added into a mixture of 100 parts of methyl difluoro (fluorosulfonyl)acetate and 250 parts of ion-exchanged water in a ice bath. The added mixture was heated and refluxed at 100° C. for 3 hours. After cooling, the cooled mixture was neutralized with 88 parts of conc. hydrochloric acid and concentrated to obtain 164.4 parts of sodium difluorosulfoacetate (containing inorganic salt, purity: 62.7%).

(2) 1.0 Part of 1,1'-carbonyldiimidazol was added to a mixture of 1.9 parts of sodium difluorosulfoacetate (purity: 62.7%) and 9.5 parts of N,N-dimethylformamide, and the added mixture was stirred for 2 hours to obtain solution (referred to as solution A). 0.2 Part of sodium hydride was added to a mixture of 1.1 parts of 3-hydroxyadamantylmethanol and 5.5 parts of N,N-dimethylfomamide, and the added mixture was stirred for 2 hours to obtain solution (referred to as solution B). The solution A was added to the solution B, and the mixture was stirred for 15 hours to obtain sodium salt of 3-hydroxy-1-adamantylmethyl difluorosulfoacetate solution. The sodium salt of 3-hydroxy-1-adamantylmethyl difluorosulfoacetate solution was used for the next step without further separation or purification.

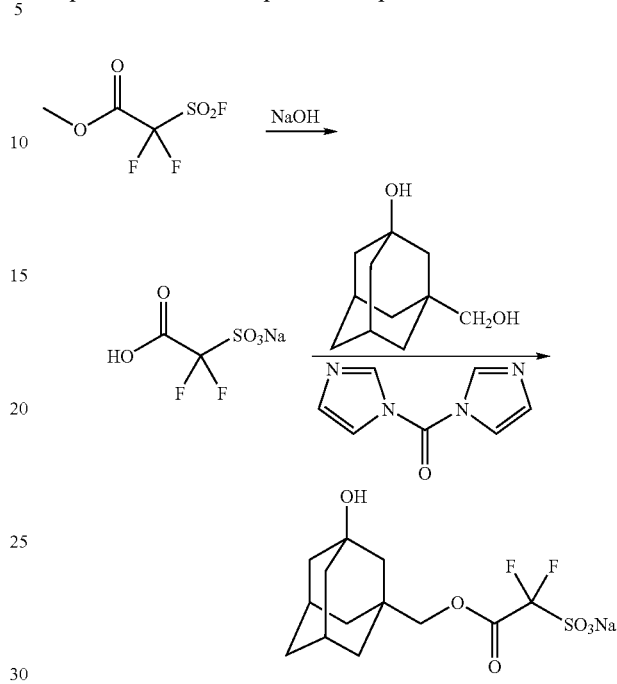

(3) 17.2 Parts of chloroform and 2.9 parts of 14.8% aqueous triphenylsulfonium chloride solution were added to the sodium salt of 3-hydroxy-1-adamantylmethyl difluorosulfoacetate solution obtained in (2). After stirred for 15 hours, resultant reaction mixture was phase-separated, and the aqueous layer was extracted with 6.5 parts of chloroform. The organic layers were combined and washed with ion-exchanged water. The washed organics layer was concentrated. 5.0 Parts of tert-butyl methyl ether was added to the concentrate. The mixture was stirred and filtered to obtain 0.2 part of triphenylsulfonium 1-((3-hydroxyadamantyl)methoxycarbonyl)difluoromethanesulfonate in the form of white solid, which is called as acid generator B2.

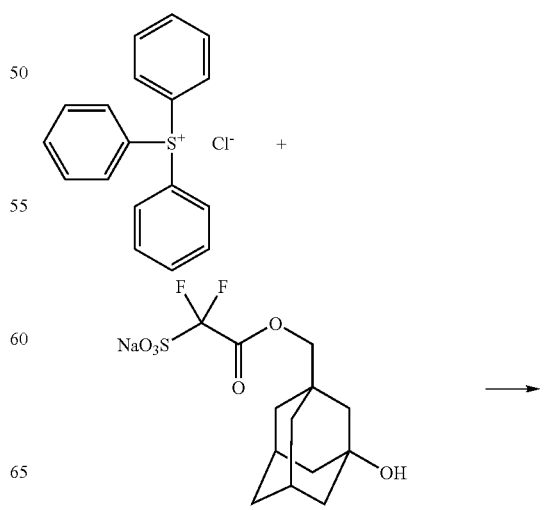

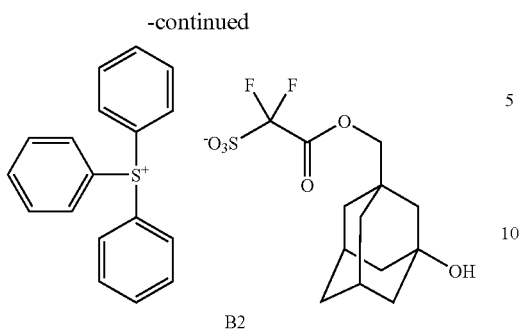

B2

$^1$H-NMR data of B2 (dimethylsulfoxide-$d_6$, Internal Standard: tetramethylsilane): d(ppm) 1.38-1.51(m, 12H); 2.07(S, 2H); 3.85(s, 2H); 4.41(s, 1H); 7.75-7.89(m, 15H) MS (ESI (+) Spectrum): M+263.07 ($C_{18}H_{15}S^+$=263.09) MS (ESI(−) Spectrum): M−339.10 ($C_{13}H_{17}F_2O_6S^-$=339.07)

REFERENTIAL EXAMPLE 1

(Synthesis of triphenylsulfonium 1-adamantyl-methoxycarbonyldifluoromethanesulfonate)

(1) 230 Parts of 30% aqueous sodium hydroxide solution was added into a mixture of 100 parts of methyl difluoro (fluorosulfonyl)acetate and 250 parts of ion-exchanged water in a ice bath. The added mixture was heated and refluxed at 100° C. for 3 hours. After cooling, the cooled mixture was neutralized with 88 parts of conc. hydrochloric acid and concentrated to obtain 164.8 parts of sodium difluorosulfoacetate (containing inorganic salt purity: 62.6%).

(2) 39.4 Parts of sodium difluorosulfoacetate purity: 62.6%), 21.0 parts of 1-adamantanemethanol and 200 part of dichloroethane were charged in a vessel, 24.0 parts of p-toluenesulfonic acid was added thereto, and the mixture was refluxed for 7 hours. After concentrating the mixture to eliminate dichloroethane, 250 parts of tert-butyl methyl ether was added thereto, and the added mixture was stirred. The stirred mixture was filtered to obtain solid. 250 parts of acetonitrile was added to the solid. The mixture was stirred and filtrated. The filtrate was concentrated to obtain 32.8 parts of sodium salt of 1-adamantylmethyl difluorosulfoacetate.

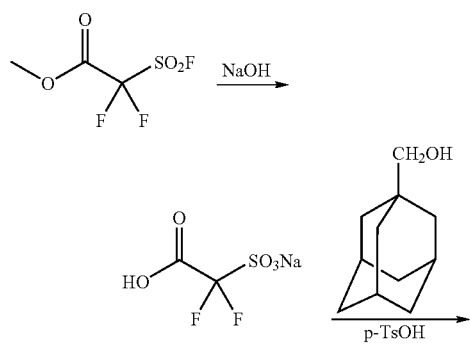

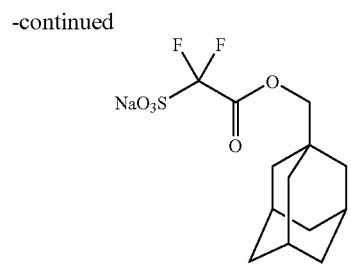

(3) 32.8 parts of sodium salt of 1-adamantylmethyl difluorosulfoacetate obtained in (2) was dissolved in 100 part of ion-exchanged water. 28.3 Parts of triphenylsulfonium chloride and 140 parts of methanol were added to the solution. After stirred for 15 hours, the stirred mixture was concentrated and extracted with 200 parts of chloroform twice. The organic layers were mixed and washed with ion-changed water. The obtained organic layer was concentrated. 300 Parts of tert-butyl methyl ether was added to the concentrate, the mixture was stirred filtered to obtain solid. The solid was dried under reduced pressure to obtain 39.7 parts of triphenylsulfonium 1-adamantylmethoxycarbonyldifluoromethanesulfonate in the form of white crystals, which is called as acid generator C1.

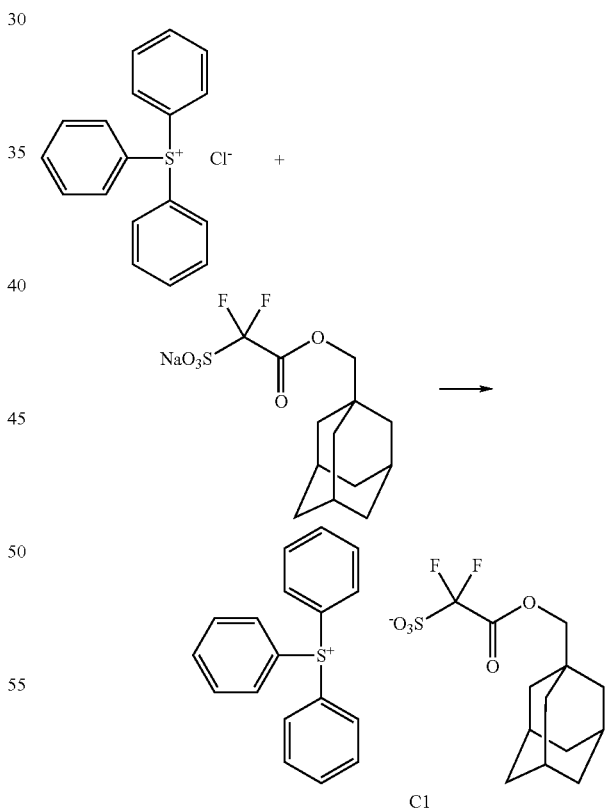

C1

$^1$H-NMR (dimethylsulfoxide-$d_6$, Internal Standard: tetramethylsilane): d(ppm) 1.52(d, 6H); 1.63(dd, 6H); 1.93(s, 3H); 3.81(s, 2H); 7.76-7.90(m, 15H) MS (ESI(+) Spectrum): M+263.2 ($C_{18}H_{15}S^+$=263.09) Cl ⊖ MS (ESI(−) Spectrum): M−323.0 ($C_{13}H_{17}F_2O_5S^-$=323.08)

RESIN SYNTHESIS EXAMPLE 1

Synthesis of Resin A1

2-Ethyl-2-adamantyl methacrylate, 3-hydroxy-1-adamantyl methacrylate and α-methacryloyloxy-γ-butyrolactone were charged at a molar ratio of 5:25:2.5 (20.0 parts:9.5 parts:7.3 parts), and methyl isobutyl ketone in twice weight based on all monomers was added, to prepare solution. To the solution was added azobisisobutyronitrile as an initiator in a ratio of 2 mol % based on all monomer molar amount, and the mixture was heated at 80° C. for about 8 hours. Then, the reaction solution was poured into large amount of heptane to cause precipitation, and this operation was repeated three tones for purification. As a result, copolymer having a weight-average molecular weight of about 9,200 was obtained. This is called resin A1.

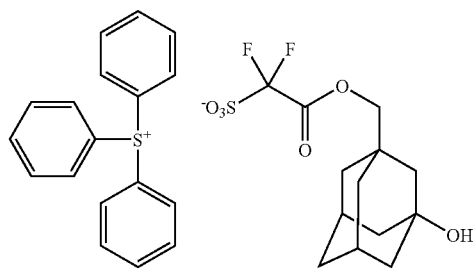

acid generator C1: 0.26 part

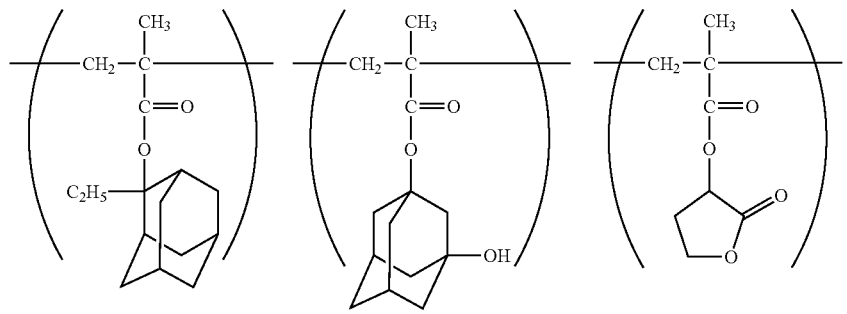

EXAMPLES 1 TO 2 AND COMPARATIVE EXAMPLES 1 TO 2

The following components were mixed and dissolved, further, filtrated through a fluorine resin filter having pore diameter of 0.2 μm, to prepare resist liquid.

<Resin>
resin A1: 10 parts

<Acid Generator>
acid generator B1: 0.27 part

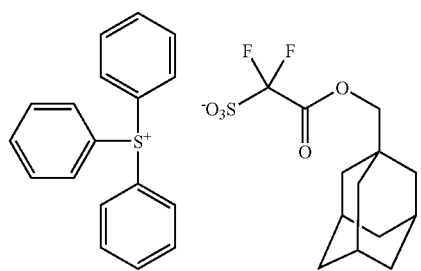

acid generator C2: triphenyl sulfonium perfluorobutane-sulfonate 0.25 part

Kind used in Examples is described in Table 1

<Quencher>
quencher Q1: 2,6-diisopropylaniline 0.0325 part

<Solvent>

| Solvent Y1: | propylene glycol monomethyl ether acetate | 51.5 parts |
| --- | --- | --- |
| | 2-heptanone | 35.0 parts |
| | γ-butyrolactone | 3.5 parts |

Silicon wafers were each coated with "ARC-29A-8", which is an organic anti-reflective coating composition available from Brewer Co., and then baked under the

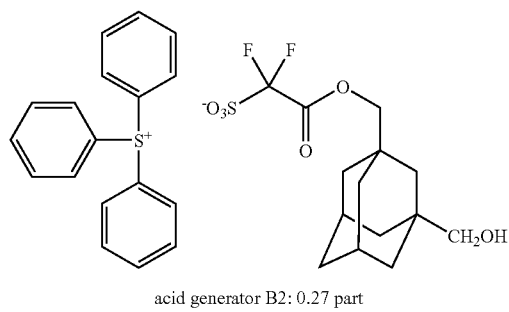

acid generator B2: 0.27 part conditions: 215° C., 60 seconds, to form a 780 Å-thick organic anti-reflective coating. Each of the resist liquids prepared as above was spin-coated over the anti-reflective coating so that the thickness of the resulting film became 0.25 µm after drying. The silicon wafers thus coated with the respective resist liquids were each prebaked on a direct hotplate at a temperature of 130° C. for 60 seconds. Using an ArF excimer stepper ("NSR ArF" manufactured by Nikon Corporation, NA=0.55, ⅔ Annular), each wafer thus formed with the respective resist film was subjected to line and space pattern exposure, with the exposure quantity being varied stepwise.

After the exposure, each wafer was subjected to post-exposure baking on a hotplate at a temperature of 130° C. for 60 seconds and then to paddle development for 60 seconds with an aqueous solution of 2.38 wt % tetramethylammonium hydroxide.

Each of a dark field pattern developed on the organic anti-reflective coating substrate after the development was observed with a scanning electron microscope, the results of which are shown in Table 1. The term "dark field pattern", as used herein, means a pattern obtained by exposure and development though a reticle comprising chromium base surface light-shielding portion) and linear glass layers (light-transmitting portion) formed in the chromium surface and aligned with each other. Thus, the dark field pattern is such that, after exposure and development, resist layer surrounding the line and space pattern remains on substrate.

Resolution:

It is expressed as the minimum size of space pattern which gave the space pattern split by the line pattern at the expose amount of the effective sensitivity. Herein, the effective sensitivity is expressed by the amount of exposure that the line pattern (light-shielding layer) and the space pattern (light-transmitting layer) become 1:1 after exposure through 0.13 µm line and space pattern mask and development.

Profile T/B

It is expressed by a ratio of top side length (referred to as T) and bottom side length (referred to as B) in line part of 0.13 µm line and space pattern. The closer to 1 the ratio is, the better the profile of its resist pattern is.

TABLE 1

| No. | Acid Generator | Resolution (µm) | Profile T/B |
|---|---|---|---|
| Example 1 | B1 | 0.12 | 1.00 |
| Example 2 | B2 | 0.12 | 0.95 |
| Comparative Example 1 | C1 | 0.13 | 0.83 |
| Comparative Example 2 | C2 | 0.13 | 0.71 |

Apparent from Table 1, The present composition gives better resist pattern in resolution and in pattern profile.

Salt (I) is suitably used for an acid generator for chemically amplified positive resist composition. The preset composition provides excellent resist pattern resolution and pattern profiles and is especially suitable for ArF excimer laser lithography, KrF excimer laser lithography and ArF immersion lithography.

What is claimed is:

1. A salt of the formula (I)

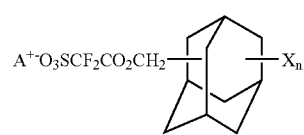

(I)

$A^{+-}O_3SCF_2CO_2CH_2$—⟨⟩—$X_n$ wherein X represents —OH or —Y—OH, n is an integer of 1 to 9, $A^+$ represents an organic counter ion, Y represents a divalent saturated aliphatic hydrocarbon group having 1 to 6 carbon atoms.

2. The salt according to claim 1, wherein $A^+$ is at least one cation selected from the group consisting of the formulae (IIa), (IIb), (IIc) and (IId), a cation of the formula (IIa)

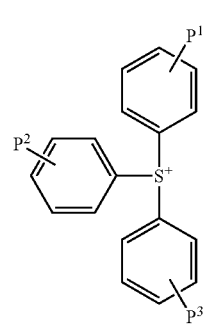

(IIa)

wherein $P^2$ to $P^3$ each independently represent hydrogen atom, hydroxyl group, alkyl group having 1 to 12 carbon atoms or alkoxy group having 1 to 12 carbon atoms, a cation of the formula (IIb)

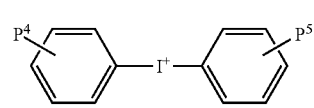

(IIb)

wherein $P^4$ and $P^5$ each independently represent hydrogen atom, hydroxyl group, alkyl group having 1 to 12 carbon atoms or alkoxy group having 1 to 12 carbon atoms, a cation of the formula (IIc)

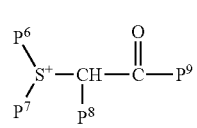

(IIc)

wherein $P^6$ and $P^7$ each independently represent alkyl having 1 to 12 carbon atoms or cycloalkyl having 3 to 12 carbon atoms, or $P^6$ and $P^7$ bond to form divalent acyclic hydrocarbon group having 3 to 12 carbon atoms which forms a ring together with the adjacent $S^+$, and at least one —$CH_2$— in the divalent acyclic hydrocarbon group is optionally substituted by —CO—, —O— or —S—, $P^8$ represents hydrogen, $P^9$ represents alkyl having 1 to 12 carbon atoms, cycloalkyl having 3 to 12 carbon atoms or aromatic ring group optionally substituted, or $P^8$ and $P^9$ bond to form divalent acyclic hydrocarbon group which forms 2-oxocycloalkyl together with the adjacent —CHCO—, and at least one —$CH_2$— in the divalent acyclic hydrocarbon group is optionally substituted by —CO—, —O— or —S—, a cation of the formula (IId)

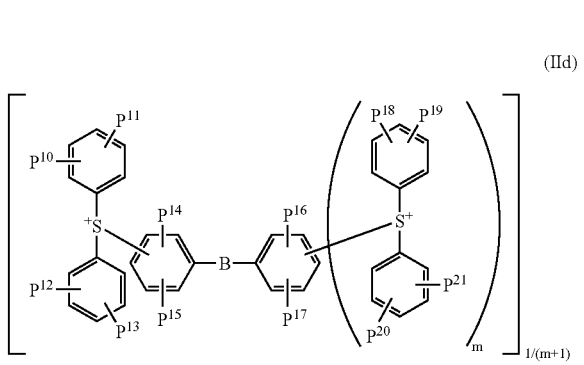

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen atom, hydroxyl group, alkyl group having 1 to 12 carbon atoms or alkoxy group having 1 to 12 carbon atoms, B represents suffix atom or oxygen atom, and m represents 0 or 1.

3. The salt according to claim 1, wherein $A^+$ is a counter ion of the formula (IIe)

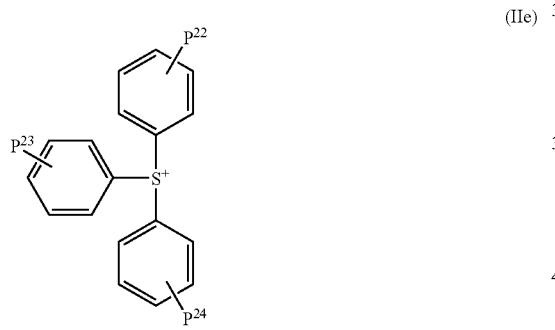

(IIe)

wherein $P^{22}$, $P^{23}$ and $P^{24}$ each independently represent hydrogen atom or alkyl group having 1 to 4 carbon atoms.

4. The salt according to claim 1, wherein X represents —OH group or —$CH_2OH$ group, and n is an integer of 1 or 2.

5. The salt according to claim 1, wherein the salt is the salt of the formula (IIIa) or (IIIb).

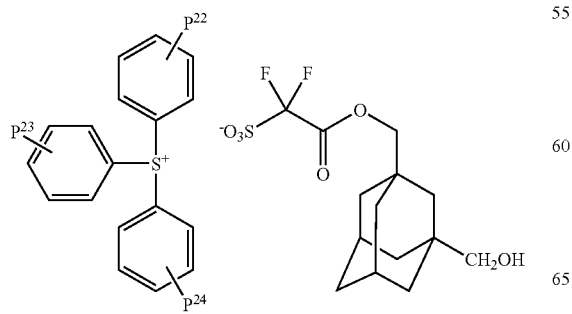

(IIIa)

-continued

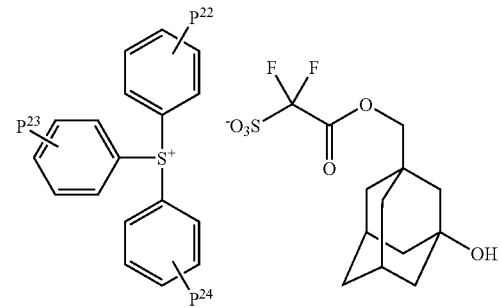

(IIIb)

wherein $P^{22}$, $P^{23}$ and $P^{24}$ each independently represent hydrogen atom or an alkyl group having 1 to 4 carbon atoms.

6. A process for producing a salt of the formula (I)

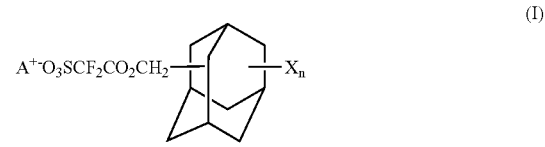

(I)

wherein X represents —OH or —Y—OH, n is an integer of 1 to 9, $A^+$ represents an organic counter ion, Y represents a divalent saturated aliphatic hydrocarbon group having 1 to 6 carbon atoms, which comprises reacting an ester of the formula (VI)

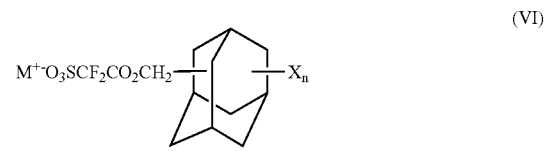

(VI)

wherein X represents —OH or —YOH, n is an integer of 1-9, Y represents a divalent saturated aliphatic hydrocarbon group having 1 to 6 carbon atoms, and M represents Li, Na, K or Ag, with an onium salt of the formula (VII)

$A^+Z^-$     (VII)

wherein $A^+$ represents an organic counter ion, and $Z^-$ represents $F^-$, $Cl^-$, $Br^-$, $I^-$, $BF_4^-$, $AsF_6^-$, $SbF_6^-$, $PF_6^-$ or $ClO_4^-$.

7. A chemically amplified resist composition comprising a salt of the formula (I)

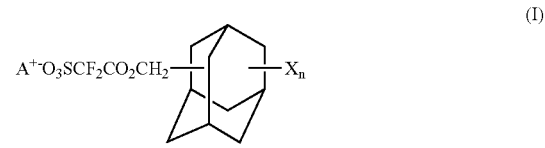

(I)

wherein X represents —OH or —Y—OH, n is an integer of 1 to 9, $A^+$ represents a counter ion, Y represents a divalent sated aliphatic hydrocarbon group having 1 to 6 carbon atoms; and a resin which contains a structural it having an acid-labile group and which itself is insoluble or poorly soluble in an alkali aqueous solution but becomes soluble in an alkali aqueous solution by the action of an acid.

8. The composition according to claim 7, wherein the resin contains a structural unit derived from a monomer having a bulky and acid-labile group.

9. The composition according to claim 8, wherein the bulky and acid-labile group is 2-alkyl-2-adamantyl group or 1-(1-adamantyl)-1-alkylalkyl group.

10. The composition according to claim 8, wherein the monomer having bulky and acid-labile group is 2-alkyl-2-adamantyl(meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate.

11. The composition according to claim 7, wherein the composition further comprises a basic compound.

12. The composition according to claim 7, wherein $A^+$ is at least one cation selected from the group consisting of the formulae (IIa), (IIb), (IIc) and (IId), a cation of the formula (IIa)

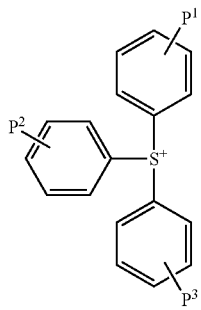

(IIa)

wherein $P^1$ to $P^3$ each independently represent hydrogen atom, hydroxyl group, alkyl group having 1 to 12 carbon atoms or alkoxy group having 1 to 12 carbon atoms, a cation of the formula (IIb)

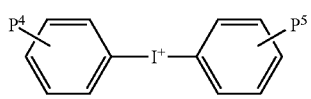

(IIb)

wherein $P^4$ and $P^5$ each independently represent hydrogen atom, hydroxyl group, alkyl group having 1 to 12 carbon atoms or alkoxy group having 1 to 12 carbon atoms, a cation of the formula (IIc)

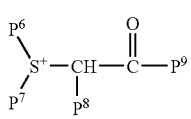

(IIc)

wherein $P^6$ and $P^7$ each independently represent alkyl having 1 to 12 carbon atoms or cycloalkyl having 3 to 12 carbon atoms, or $P^6$ and $P^7$ bond to form divalent acyclic hydrocarbon group having 3 to 12 carbon atoms which forms a ring together with the adjacent $S^+$, and at least one —CH$_2$— in the divalent acyclic hydrocarbon group is optionally substituted by —CO—, —O— or —S—, $P^8$ represents hydrogen, $P^9$ represents alkyl having 1 to 12 carbon atoms, cycloalkyl having 3 to 12 carbon atoms or aromatic ring group optionally substituted, or $P^8$ and $P^9$ bond to form divalent acyclic hydrocarbon group which forms 2-oxocycloalkyl together with the adjacent —CHCO—, and at least one —CH$_2$— in the divalent acyclic hydrocarbon group is optionally substituted by —CO—, —O— or —S—, a cation of the formula (IId)

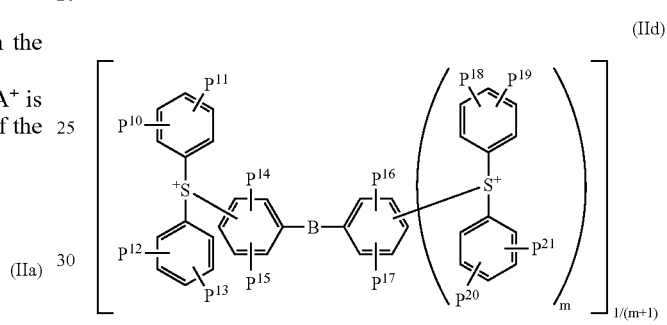

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen atom, hydroxyl group, alkyl group having 1 to 12 carbon atoms or alkoxy group having 1 to 12 carbon atoms, B represent sulfur atom or oxygen atom, and m represents 0 or 1.

13. The composition according to claim 7, wherein $A^+$ is a counter ion of the formula (IIe)

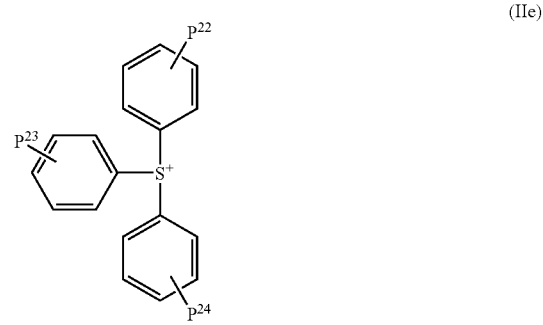

(IIe)

wherein $P^{22}$, $P^{23}$ and $P^{25}$ each independently represent hydrogen atom or alkyl group having 1 to 4 carbon atoms.

14. The composition according to claim 7, wherein X represents —OH group or —CH$_2$OH group, and n is an integer of 1 or 2.

15. The composition according to claim 7, wherein the salt is the salt of the formula (IIIa) or (IIIb)
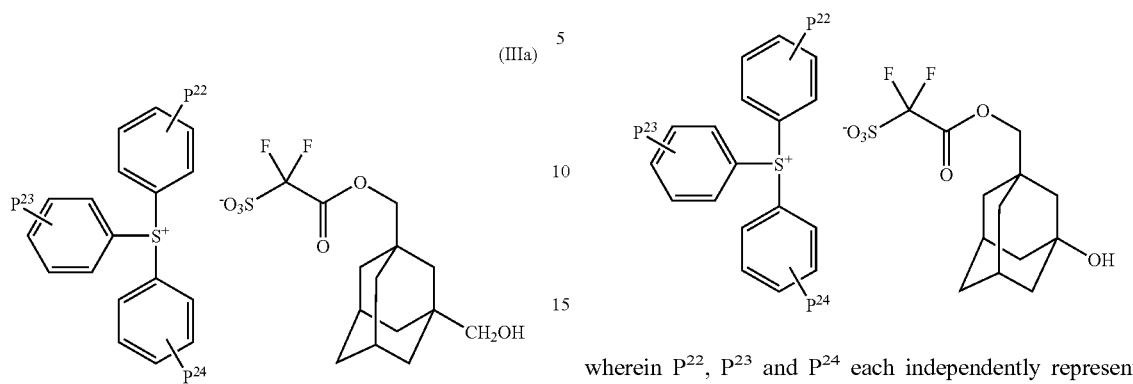
wherein $P^{22}$, $P^{23}$ and $P^{24}$ each independently represent a hydrogen atom or an alkyl group having 1 to 4 carbon atoms.
* * * * *